US008404144B2

(12) United States Patent
Abuelyaman et al.

(10) Patent No.: US 8,404,144 B2
(45) Date of Patent: Mar. 26, 2013

(54) COMPOSITIONS INCLUDING POLYMERIZABLE BISPHOSPHONIC ACIDS AND METHODS

(75) Inventors: Ahmed S. Abuelyaman, Woodbury, MN (US); Gail S. Boardman, Woodbury, MN (US); Brian A. Shukla, Woodbury, MN (US); Steven M. Aasen, Woodbury, MN (US); Sumita B. Mitra, West St. Paul, MN (US); Markus Mikulla, Andechs-Frieding (DE); David K. Cinader, Jr., Walnut, CA (US)

(73) Assignee: 3M Innovative Properties Company, Saint Paul, MN (US)

( * ) Notice: Subject to any disclaimer, the term of this patent is extended or adjusted under 35 U.S.C. 154(b) by 613 days.

(21) Appl. No.: 12/275,954

(22) Filed: Nov. 21, 2008

(65) Prior Publication Data

US 2009/0075239 A1 Mar. 19, 2009

Related U.S. Application Data

(62) Division of application No. 10/729,497, filed on Dec. 5, 2003, now abandoned.

(60) Provisional application No. 60/437,106, filed on Dec. 30, 2002.

(51) Int. Cl.
*A61K 6/00* (2006.01)
*A61K 6/02* (2006.01)
*A61K 6/083* (2006.01)
*A61C 5/00* (2006.01)

(52) U.S. Cl. .......................... 252/79.1; 433/215; 433/216

(58) Field of Classification Search ................. 252/79.1; 433/215, 216
See application file for complete search history.

(56) References Cited

U.S. PATENT DOCUMENTS

| | | | |
|---|---|---|---|
| 3,655,605 A | 4/1972 | Smith | |
| 3,797,690 A | 3/1974 | Taylor | |
| 4,016,124 A | 4/1977 | Crisp et al. | |
| 4,054,598 A | 10/1977 | Blum et al. | |
| 4,070,321 A | 1/1978 | Goretta et al. | |
| 4,089,830 A | 5/1978 | Tezuka et al. | |
| 4,143,018 A | 3/1979 | Crisp et al. | |
| 4,204,978 A | 5/1980 | Ibsen et al. | |
| 4,259,075 A | 3/1981 | Yamauchi et al. | |
| 4,259,117 A | 3/1981 | Yamauchi et al. | |
| 4,267,108 A | 5/1981 | Blum et al. | |
| 4,298,738 A | 11/1981 | Lechtken et al. | |
| 4,302,381 A | 11/1981 | Omura et al. | |
| 4,304,734 A | 12/1981 | Jary et al. | |
| 4,324,744 A | 4/1982 | Lechtken et al. | |
| 4,327,039 A | 4/1982 | Blum et al. | |
| 4,342,677 A | 8/1982 | Muramatsu et al. | |
| 4,347,233 A | 8/1982 | Yamauchi et al. | |
| 4,356,296 A | 10/1982 | Griffith et al. | |
| 4,360,605 A | 11/1982 | Schmitt et al. | |
| 4,368,403 A | 1/1983 | Lewis | |
| 4,376,835 A | 3/1983 | Schmitt et al. | |
| 4,383,052 A | 5/1983 | Higo et al. | |
| 4,385,109 A | 5/1983 | Lechtken et al. | |
| 4,407,761 A | 10/1983 | Blum et al. | |
| 4,499,251 A | 2/1985 | Omura et al. | |
| 4,503,169 A | 3/1985 | Randklev | |
| 4,507,407 A | 3/1985 | Kluger | |
| 4,526,728 A | 7/1985 | Finke et al. | |
| 4,537,940 A | 8/1985 | Omura et al. | |
| 4,539,382 A | 9/1985 | Omura et al. | |
| 4,612,384 A | 9/1986 | Omura et al. | |
| 4,621,077 A | 11/1986 | Rosini et al. | |
| 4,642,126 A | 2/1987 | Zador et al. | |
| 4,648,843 A | 3/1987 | Mitra | |
| 4,650,847 A | 3/1987 | Omura et al. | |
| 4,652,274 A | 3/1987 | Boettcher et al. | |
| 4,665,217 A | 5/1987 | Reiners et al. | |
| 4,678,436 A | 7/1987 | Kondo | |
| 4,687,767 A | 8/1987 | Bosies et al. | |
| 4,695,251 A | 9/1987 | Randklev | |
| 4,710,523 A | 12/1987 | Lechtken et al. | |
| 4,719,149 A | 1/1988 | Aasen et al. | |
| 4,737,593 A | 4/1988 | Ellrich et al. | |
| 4,752,338 A | 6/1988 | Reiners et al. | |
| 4,755,620 A | 7/1988 | Iwamoto et al. | |
| 4,792,632 A | 12/1988 | Ellrich et al. | |
| 4,814,514 A | 3/1989 | Yokota et al. | |
| 4,816,495 A | 3/1989 | Blackwell et al. | |
| 4,872,936 A | 10/1989 | Engelbrecht | |
| 4,922,007 A | 5/1990 | Kieczykowski et al. | |
| 4,939,283 A | 7/1990 | Yokota et al. | |
| 5,019,651 A | 5/1991 | Kieczykowski | |
| 5,026,902 A | 6/1991 | Fock et al. | |
| 5,055,497 A | 10/1991 | Okada et al. | |
| 5,063,257 A | 11/1991 | Akahane et al. | |
| 5,076,844 A | 12/1991 | Fock et al. | |

(Continued)

FOREIGN PATENT DOCUMENTS

DE 273 846 11/1929
DE 2537 463 A1 4/1976

(Continued)

OTHER PUBLICATIONS

Palma, R.G., Turbino, M.L., Watson, E., Powers, J.M., "Bond Strength to dentin with artificial carious lesion: influence of caries detecting dye" American Journal of Dentistry, vol. 11, No. 3, 1998, pp. 128-130, XP008055059 abstract.

Kazemi, R.B., Meiers, J.J., Peppers, K., "Effect of caries disclosing agents on bond strengths of total etch and self-etching primer dentin bonding systems to resin composite", Operative Dentistry, vol. 27 No. 3, 2002, pp. 238-242, XP008504961, whole document.

TYRIAN SPE Universal Self-Priming Etchant, TYRIAN SPE General Information, BISCO, Inc., Schaumburg, IL [retrieved from the internet on Jul. 7, 2004] URLhttp://www.bisco.com/instructions/tyrianspe_inst_print.asp 8 pages.

(Continued)

*Primary Examiner* — Lezah Roberts
(74) *Attorney, Agent, or Firm* — Carlos M. Téllez; 3M Innovative Properties Company

(57) ABSTRACT

The present invention is directed to compositions containing one or more polymerizable bisphosphonic acids and optionally one or more additional polymerizable components.

43 Claims, No Drawings

U.S. PATENT DOCUMENTS

| | | |
|---|---|---|
| 5,130,347 A | 7/1992 | Mitra |
| 5,154,762 A | 10/1992 | Mitra et al. |
| 5,172,809 A | 12/1992 | Jacobs et al. |
| 5,180,757 A | 1/1993 | Lucey |
| 5,227,413 A | 7/1993 | Mitra |
| 5,254,198 A | 10/1993 | Kawashima et al. |
| 5,256,447 A | 10/1993 | Oxman et al. |
| 5,324,862 A | 6/1994 | Yokota et al. |
| 5,332,854 A | 7/1994 | Yokota et al. |
| 5,338,769 A | 8/1994 | Miyamoto |
| 5,354,827 A | 10/1994 | Miller et al. |
| 5,367,002 A | 11/1994 | Huang et al. |
| 5,501,727 A | 3/1996 | Wang et al. |
| 5,510,517 A | 4/1996 | Dauer et al. |
| 5,520,725 A | 5/1996 | Kato et al. |
| 5,525,648 A | 6/1996 | Aasen et al. |
| 5,530,038 A | 6/1996 | Yamamoto et al. |
| 5,545,676 A | 8/1996 | Palazzotto et al. |
| 5,554,030 A | 9/1996 | Ario et al. |
| 5,575,645 A | 11/1996 | Jacobs et al. |
| 5,593,303 A | 1/1997 | Cohen et al. |
| 5,608,042 A | 3/1997 | Himeno |
| 5,629,361 A | 5/1997 | Nakabayashi et al. |
| 5,645,429 A | 7/1997 | Blackwell et al. |
| 5,648,491 A | 7/1997 | Dauer et al. |
| 5,658,963 A | 8/1997 | Qian et al. |
| 5,710,194 A | 1/1998 | Hammesfahr et al. |
| 5,766,012 A | 6/1998 | Rosenbaum et al. |
| 5,834,532 A | 11/1998 | Yamamoto et al. |
| 5,856,373 A | 1/1999 | Kaisaki et al. |
| 5,859,089 A | 1/1999 | Qian |
| 5,871,360 A | 2/1999 | Kato |
| 5,919,836 A | 7/1999 | Reinhardt |
| 5,919,846 A | 7/1999 | Batlaw |
| 5,925,715 A | 7/1999 | Mitra |
| 5,962,550 A | 10/1999 | Akahane et al. |
| 5,965,632 A | 10/1999 | Orlowski et al. |
| 5,980,253 A | 11/1999 | Oxman et al. |
| 5,980,868 A | 11/1999 | Homola |
| 6,004,390 A | 12/1999 | Pflug et al. |
| 6,030,606 A | 2/2000 | Holmes |
| 6,050,815 A | 4/2000 | Adam et al. |
| 6,084,004 A | 7/2000 | Weinmann et al. |
| 6,089,861 A | 7/2000 | Kelly et al. |
| 6,126,922 A | 10/2000 | Mitra et al. |
| 6,172,131 B1 | 1/2001 | Moszner et al. |
| 6,174,935 B1 | 1/2001 | Matsunae et al. |
| 6,187,833 B1 | 2/2001 | Oxman et al. |
| 6,187,836 B1 | 2/2001 | Oxman et al. |
| 6,213,767 B1 | 4/2001 | Dixon et al. |
| 6,217,644 B1 | 4/2001 | Matsunae et al. |
| 6,251,963 B1 | 6/2001 | Kohler et al. |
| 6,306,926 B1 | 10/2001 | Bretscher et al. |
| 6,309,215 B1 | 10/2001 | Phan et al. |
| 6,331,080 B1 | 12/2001 | Cole et al. |
| 6,350,839 B2 | 2/2002 | Moszner et al. |
| 6,355,704 B1 | 3/2002 | Nakatsuka et al. |
| 6,387,979 B1 | 5/2002 | Hino |
| 6,387,981 B1 | 5/2002 | Zhang et al. |
| 6,387,982 B1 | 5/2002 | Blackwell |
| 6,444,725 B1 | 9/2002 | Trom et al. |
| 6,458,868 B1 | 10/2002 | Okada et al. |
| 6,472,454 B1 | 10/2002 | Qian |
| 6,482,871 B1 | 11/2002 | Aasen et al. |
| 6,506,816 B1 | 1/2003 | Ario et al. |
| 6,528,555 B1 | 3/2003 | Nikutowski et al. |
| 6,565,873 B1 | 5/2003 | Shefer et al. |
| 6,566,413 B1 | 5/2003 | Weinmann et al. |
| 6,572,693 B1 | 6/2003 | Wu et al. |
| 6,575,752 B1 | 6/2003 | Pflug |
| 6,624,236 B1 | 9/2003 | Bissinger et al. |
| 6,669,927 B2 | 12/2003 | Trom et al. |
| 6,691,715 B2 | 2/2004 | Matz et al. |
| 6,765,038 B2 | 7/2004 | Mitra |
| 6,830,450 B2 | 12/2004 | Knopp et al. |
| 6,869,984 B2 | 3/2005 | Kawashima et al. |
| 6,905,672 B2 | 6/2005 | Rajaiah |
| 6,916,858 B2 | 7/2005 | Kojima et al. |
| 6,939,901 B2 | 9/2005 | Nakatsuka |
| 6,960,079 B2 | 11/2005 | Brennan et al. |
| 6,982,288 B2 | 1/2006 | Mitra et al. |
| 6,994,551 B2 | 2/2006 | Wang et al. |
| 7,090,721 B2 | 8/2006 | Craig et al. |
| 7,090,722 B2 | 8/2006 | Budd et al. |
| 7,129,281 B2 | 10/2006 | Fujiwara |
| 7,134,875 B2 | 11/2006 | Oxman |
| 7,137,812 B2 | 11/2006 | Cleary |
| 7,156,911 B2 | 1/2007 | Kangas et al. |
| 7,173,074 B2 | 2/2007 | Mitra et al. |
| 7,186,950 B1 | 3/2007 | Fisher |
| 7,250,452 B2 | 7/2007 | Falsafi |
| 7,262,228 B2 | 8/2007 | Oxman |
| 7,374,420 B2 | 5/2008 | Brennan |
| 7,473,096 B2 | 1/2009 | Cinader, Jr. |
| 7,541,393 B2 | 6/2009 | Mitra |
| 7,632,098 B2 | 12/2009 | Falsafi et al. |
| 7,699,605 B2 | 4/2010 | Aasen et al. |
| 7,841,464 B2 | 11/2010 | Cinader, Jr. |
| 7,910,632 B2 | 3/2011 | Cinader, Jr. |
| 2001/0044513 A1 | 11/2001 | Moszner et al. |
| 2002/0015682 A1 | 2/2002 | Stangel et al. |
| 2002/0016384 A1 | 2/2002 | Moszner et al. |
| 2003/0060536 A1 | 3/2003 | Spange |
| 2003/0087986 A1 | 5/2003 | Mitra |
| 2003/0166737 A1 | 9/2003 | Dede et al. |
| 2003/0166740 A1 | 9/2003 | Mitra et al. |
| 2003/0166816 A1 | 9/2003 | Bissinger et al. |
| 2003/0181541 A1 | 9/2003 | Wu et al. |
| 2003/0187092 A1 | 10/2003 | Fujiwara |
| 2003/0195273 A1 | 10/2003 | Mitra et al. |
| 2003/0196914 A1 | 10/2003 | Tzou et al. |
| 2003/0198914 A1 | 10/2003 | Brennan et al. |
| 2004/0110864 A1 | 6/2004 | Hecht et al. |
| 2004/0151691 A1 | 8/2004 | Oxman et al. |
| 2004/0192804 A1 | 9/2004 | Kura |
| 2004/0206932 A1 | 10/2004 | Abuelyaman |
| 2005/0074716 A1 | 4/2005 | Cleary et al. |
| 2005/0113477 A1 | 5/2005 | Oxman et al. |
| 2005/0133384 A1 | 6/2005 | Cinader |
| 2005/0154081 A1 | 7/2005 | Yin |
| 2005/0175965 A1 | 8/2005 | Craig et al. |
| 2005/0175966 A1 | 8/2005 | Falsafi et al. |
| 2005/0176844 A1 | 8/2005 | Aasen et al. |
| 2005/0256223 A1 | 11/2005 | Kolb et al. |
| 2005/0277084 A1 | 12/2005 | Cinader et al. |
| 2006/0030637 A1 | 2/2006 | Mitra |
| 2006/0069181 A1 | 3/2006 | Thalacker |
| 2006/0084026 A1 | 4/2006 | Cinader et al. |
| 2007/0039519 A1 | 2/2007 | Kangas et al. |
| 2007/0207094 A1 | 9/2007 | Oxman |
| 2007/0248927 A1 | 10/2007 | Luchterhandt et al. |
| 2008/0096150 A1 | 4/2008 | Cinader |
| 2008/0299519 A1 | 12/2008 | Craig et al. |
| 2009/0011388 A1 | 1/2009 | Craig |
| 2009/0030101 A1 | 1/2009 | Wang et al. |
| 2009/0075239 A1 | 3/2009 | Abuelyaman |

FOREIGN PATENT DOCUMENTS

| | | |
|---|---|---|
| DE | 35 36 076 A1 | 4/1987 |
| DE | 199 18 974 | 12/1999 |
| DE | 695 18 037 T2 | 3/2001 |
| EP | 0 115 812 A2 | 8/1984 |
| EP | 0 115 948 A1 | 8/1984 |
| EP | 0 115 948 B1 | 8/1984 |
| EP | 0 173 567 | 3/1986 |
| EP | 0 184 095 A2 | 6/1986 |
| EP | 0 184 095 B1 | 6/1986 |
| EP | 0 201 031 | 11/1986 |
| EP | 0 201 778 A1 | 11/1986 |
| EP | 0 201 778 B1 | 11/1986 |
| EP | 0 206 810 A2 | 12/1986 |
| EP | 0 206 810 B1 | 12/1986 |
| EP | 0 237 233 A2 | 9/1987 |
| EP | 323120 | 7/1989 |
| EP | 0 201 031 | 8/1989 |
| EP | 0 335 645 A2 | 10/1989 |
| EP | 0 335 645 A3 | 10/1989 |

| | | |
|---|---|---|
| EP | 0 335 645 B1 | 10/1989 |
| EP | 0 351 076 A2 | 1/1990 |
| EP | 0 351 076 B1 | 1/1990 |
| EP | 0 373 384 | 6/1990 |
| EP | 0 373 384 | 10/1992 |
| EP | 0 509 516 A2 | 10/1992 |
| EP | 0 509 516 A3 | 10/1992 |
| EP | 0 509 516 B1 | 10/1992 |
| EP | 0 537 774 A1 | 4/1993 |
| EP | 0 537 774 B1 | 4/1993 |
| EP | 0 323 012 B1 | 5/1993 |
| EP | 0 661 034 A1 | 7/1995 |
| EP | 0 661 034 B1 | 7/1995 |
| EP | 0 712 622 A1 | 5/1996 |
| EP | 0 712 622 B1 | 5/1996 |
| EP | 0 897 710 | 2/1999 |
| EP | 0 661 034 A1 | 3/1999 |
| EP | 1 051 961 A1 | 11/2000 |
| EP | 1051961 | 11/2000 |
| EP | 1 121 924 A2 | 8/2001 |
| EP | 1 141 094 | 7/2002 |
| EP | 1 287 805 A1 | 3/2003 |
| EP | 1 346 717 A1 | 9/2003 |
| GB | 2 251 861 | 7/1992 |
| JP | 59015468 | 1/1984 |
| JP | 59-135272 | 8/1984 |
| JP | 60-089752 | 5/1985 |
| JP | 61-151104 | 7/1986 |
| JP | 06-041162 | 2/1994 |
| JP | 7330530 | 12/1995 |
| JP | 10-512567 | 12/1998 |
| JP | 11139920 | 5/1999 |
| JP | 2000204010 | 7/2000 |
| JP | 2001072936 | 3/2001 |
| JP | 2004182661 | 7/2004 |
| JP | 2005-008537 | 1/2005 |
| WO | WO 98/03443 | 1/1998 |
| WO | WO 98/46198 | 10/1998 |
| WO | WO 00/30591 | 6/2000 |
| WO | WO 00/38619 | 6/2000 |
| WO | WO 00/4292 | 7/2000 |
| WO | WO 01/07444 | 2/2001 |
| WO | WO 01/30304 | 5/2001 |
| WO | WO 01/30305 | 5/2001 |
| WO | WO 01/30306 | 5/2001 |
| WO | WO 01/30307 | 5/2001 |
| WO | WO 01/92271 | 5/2001 |
| WO | WO 0138449 | 5/2001 |
| WO | WO 02/02057 | 1/2002 |
| WO | WO 02/11642 | 2/2002 |
| WO | WO 02/092021 | 11/2002 |
| WO | WO 03/013444 | 2/2003 |
| WO | WO 03/063804 | 8/2003 |
| WO | WO 03/068174 A1 | 8/2003 |
| WO | WO 2005/004819 A | 1/2005 |
| WO | WO 2005/018581 A | 3/2005 |
| WO | WO 2006/014597 | 2/2006 |
| WO | WO 2007/075666 | 7/2007 |

OTHER PUBLICATIONS

Hodges et al., Journal of Orthodontics, "Unusual Indelible Enamel Staining Following Fixed Appliance Treatment", vol. 27, pp. 303-306 (2000).
Written Opinion of ISR for PCT/US2005/024291.
Written Opinion of ISR for PCT/US2004/025936.
IPER for PCT/US03/31387.
Written Opinion of ISR for PCT/US2005/028536.
U.S. Appl. No. 60/586,326, filed Jul. 8, 2004, entitled "Dental Methods, Compositions, and Kits Including Acid-sensitive Dyes".
U.S. Appl. No. 60/600,658, filed Jul. 8, 2004, entitled "Dental Methods, Compositions including a Plurality of Acidic Compounds".
U.S. Appl. No. 60/600,558, filed Aug. 11, 2004, entitled Dental Methods, Compositions, and Kits Including Acid-sensitive Dyes.
U.S. Appl. No. 60/494,603, filed Aug. 12, 2003, entitled "Dental Compositions and Methods".
Mathis et al., Journal of Dental Research, "Properties of a New Glass Ionomer/Composite Resin Hybrid Restorative", Abstract No. 51, vol. 66, pp. 113 (1987).
Banerjee S. et al.; "Polymer Precipitation Using a Micellar Nonsolvent: The Role of Surfactant-Polymer Interactions and the Development of a Microencapsulation Technique"; Ind. Eng. Chem. Res., vol. 35, No. 9 (1996) pp. 3100-3107.
Buonocore, M. et al.; "A Report On a Resin Composition Capable of Bonding to Human Dentin Surfaces"; J. Dent. Res.,vol. 35, No. 6 (1956) pp. 846-851.
Floyd J. Green; "The Sigma-Aldrich Handbook of Stains, Dyes and Indicators"; Aldrich Chemical Company, Inc.; 1990; pp. Cover, publication and Table of Contents.
Holmberg et al.; "Chapter 6—Microemulsions"; Surfactants and Polymers in Aqueous Solution; Second Edition, John Wiley & Sons, pp. 139-155 (2003: Reprinted with corrections in 2004).
ISO Standard 4049—Dentistry—Polymer-based filling, restorative and luting materials; Ref. No. ISO 4049:2000(E); (2000).
ISO Standard 7489—Dental glass polyalkenoate cements; Ref. No. ISO 7489-1986 (E); First Edition May 5, 1986
ISO Standard 9917-1—Dentistry—Water-based cements; Ref. No. ISO 9917-1:2003(E); First Edition Nov. 1, 2003.
Leung, R. et al.; "Chapter 9—Microemulsions: Formation, Structure, Properties, and Novel Applications"; Surfactants in Chemical/Process Engineering; Marcel Dekker, Inc. New York and Basel; Title, publication and pp. 315-367 (1988).
Ostrovsky, M. et al.; "Mechanism of Microemulsion Formation in Systems with Low Interfacial Tension: Occurrence, Properties, and Behavior of Microemulsions"; Journal of Colloid and Interface Science, vol. 102, No. 1, Nov. 1984 pp. 206-226.
Overbeek, J. et al.; "Microemulsions" Surfactants; Edited by Th. F. Tadros; Academic Press, Inc. London; 1984; Cover, publication, Table of Contents and pp. 111-132.
Ruckenstein, E. et al.; "Stability of Microemulsions"; J. Chem. Soc. Faraday Trans II, vol. 71; (1975); pp. 1690-1707.
Rumphorst, A. et al.; "Examination of the Formulation of an Innovative Single-Component Bonding System"; Signature; vol. 6, No. 1; Sep. 2000; pp. 1-3.
Safran, S. et al.; "Phase Diagrams for Microemulsions"; Physical Review Letters; vol. 50, No. 24; Jun. 13, 1983; pp. 1930-1933.
Xu, X et al.; "Formation of Novel Organogels by the Addition of Phenols to AOT Micelles in Isooctane"; J. Phys. Chem.; vol. 97, No. 43; Oct. 28, 1993 pp. Cover, title and pp. 11350-11353.
Dyba et al., J. Chem. Soc. Dalton Trans. (1996). 1119-1123.
Gumienna-Kontecka et al., J. Inorg. Biochem. 89 (2002), 13-17.
Kieczykowski et al., J. Org. Chem. (1995), 60, 8310-8312.
Mathis et al., "Properties of a New Glass Ionomer/Composite Resin Hybrid Restorative,".
Abstract No. 51, J. Dent. Res., 66: 113 (1987).
Mosner et al., Mactomol. Chem. Phys. 200 (1999), 1062-67.
Technical Product Profile, "3M ESPE Adper™ Prompt™ L-Pop™ and Adper™ Prompt™ Self-Etch adhesives," Title Page, Table of contents, and pp. 3, 5-23, and Publication p., 3M IPC (2002).
Tromelin et al., Phosphorus Sufur Relat. Elem. 27, (1986), 301.
Alberti, "Cationic Dyes for Acrylic Fibers IV. Catonic Dyes from 6-Methyl-2-(p-Aminophenyl) Benzothiazole and Angular 2-Aminonapthtothiazoles", Chimica e L'Industria, 1974, vol. 56, No. 10, pp. 684-686.
Billmeyer, Principles of Color Technology, Second Edition, New York, NY (1981).
"Blue No. 403", [online], [retrieved from the internet on Aug. 24, 2006], <http://www02.so-net.ne.jp/~tombo/ci/b403e.htm>, 1 page.
Clinpro Sealant, Technical Product Profile, No. 70/2009-2265-9, 3M ESPE (2001), pp. 1-20.
"Color Center, Color Handbook, Anthrapyrimidine", Special Chem Innovations and Solutions [on line], [retrieved from the internet on Aug. 24, 2006], <http://www.specialchem4coatings.com/tc/color-handbook>, 2 pages.
"Colour Index", The Society of Dyers and Colourists [on line], [retrieved from the internet on Nov. 29, 2005], <http://www.sdc.org.uk/publications/ci4classes.htm>, 2 pages.
"Disperse Dyes", Technology Information Forecasting and Assessment Council, Asian and Pacific Centre for Transfer of Technology, [on line], [retrieved from the internet on Nov. 28, 2005], <http://www.tifac.org.in/offer/tsw/apctt10.htm>, 4 pages.

"Dye Classes for Principal Applications," Dr. Klaus Hunger (author and editor), Wiley Interscience Online Book, [retrieved from the internet on Nov. 29, 2005], <http://www.3.interscience.wiley.com/cgi-bin/summary/107642439/SUMMARY>, 3 pages.

"Epochem Products 2004", Epochem Co., Ltd, <http://www.Epochem.com>, 2002-2004, pp. 1-25.

"Essay: Dyes and Dyeing", Supplement to Experiment 9, Univ. of CO, Boulder, Dept. of Chem. and Biochem. 2006, pp. 63-70.

Freeman, "Synthetic Dyes Based on Toxicological Considerations", National Textile Center Annual Report, Sep. 1993, pp. 167-176.

Green, The Sigma-Aldrich Handbook of Stains, Dyes, and Indicators, Aldrich Chemical Company, pp. 284, 290, 291, 398, 647, 660, (1990).

Heitzman, "Organic Yellows for Plastics", Sun Chemical Corporation, Performance Plastics Business Unit, pp. 12-15.

"One-Up Bond F" literature, Tokuyama Corp., Product description and general information, 1 page, [date unknown but believed to be prior to the date of the filing of the present application].

Patel, "Synthesis of Monoazo Disperse Dyes from 2-Amino-4-Methylbenzothiazole and Their Application on Polyester Fiber", Oriental Journal Chemistry, 1996, vol. 12, No. 2, pp. 193-195.

StainsFile, "Anthraquinone Dyes", [retrieved from the internet on Nov. 28, 2005], <http://stasfile.info.StainsFile/dyes/class/clsanthq.htm>, 1 page.

The Complete Technology Book on Dyes & Dye Intermediates, National Institute of Industrial Research [on line], [retrieved from the internet on Nov. 29, 2005], <http://www.niir.org>, pp. 1-42. [ISBN: 81-86623-79-5].

Twenty-first Report of the Interagency Testing Committee to the Administrator; Receipt of Report and Request for Comments Regarding Priority List of Chemicals, Notices, Federal Register, vol. 52, No. 224, Nov. 1987, pp. 44830-44837.

International Search Report for Int'l Appln. No. PCT/US2003/041487, 3 pages.

International Search Report for Int'l Appln. No. PCT/US2004/025936, 3 pages.

International Search Report for Int'l Appln. No. PCT/US2005/024291, 4 pages.

International Search Report for Int'l Appln. No. PCT/US2005/028536, 4 pages.

International Search Report for Int'l Appln. No. PCT/US2007/087192, 3 pages.

COMPOSITIONS INCLUDING POLYMERIZABLE BISPHOSPHONIC ACIDS AND METHODS

CROSS-REFERENCE TO RELATED APPLICATIONS

The present application is a divisional of U.S. application Ser. No. 10/729,497, filed on Dec. 5, 2003 now abandoned, which claims priority to U.S. Provisional Patent Application Ser. No. 60/437,106, filed on Dec. 30, 2002, which is incorporated herein by reference.

TECHNICAL FIELD

The present invention is directed toward compositions containing polymerizable bisphosphonic acids that can be used in a variety of applications, particularly medical, dental, and orthodontic applications, for example. Such compositions are particularly useful as etchants, especially self-etching primers and self-etching adhesives, to promote adhesion of dental restoratives, orthodontic appliances, etc., to dental structures.

BACKGROUND

The restoration of decayed dental structures including caries, decayed dentin or decayed enamel, is often accomplished by the sequential application of a dental adhesive and then a dental material (e.g., a restorative material) to the relevant dental structures. Similarly, adhesives are used in the bonding of orthodontic appliances (generally also utilizing an orthodontic adhesive) to a dental structure. Often various pretreatment processes are used to promote the bonding of adhesives to dentin or enamel, for example. Typically, such pretreatment steps include etching using, for example, inorganic or organic acids, followed by priming to improve the bonding between the tooth structure and the overlying adhesive.

Whether for application of dental restoratives (e.g., composites, fillings, sealants, inlays, onlays, crowns, bridges, etc.) or orthodontic appliances to a tooth structure, the etchants, primers, and adhesives are typically applied in a step-wise fashion. Often between such steps, one or more rinsing and drying steps are used. As a result, dental restoration and the application of orthodontic appliances typically involve multi-step procedures.

To simplify conventional restorative and/or orthodontic procedures, for example, it would be desirable to provide a single composition that accomplishes both etching and priming. Thus, there is a need for a self-etching primer, particularly a self-etching dental primer, for improved bonding of an adhesive (e.g., a dental adhesive) to a substrate surface (e.g., dental structure, such as dentin, enamel, bone, or other hard tissue) and that could eliminate the conventional post-etching rinsing and drying steps. Furthermore, there is still a need for new compositions that can serve as self-etching adhesives, i.e., a single-composition adhesive with priming and etching properties that can be applied in a single pretreatment step. Preferred embodiments of the present invention meet some of these needs.

SUMMARY

The present invention is directed to compositions containing one or more polymerizable bisphosphonic acids, salts thereof, or combinations thereof. Such compositions are useful in a variety of medical and dental applications, for example, as etchants, particularly self-etching primers (i.e., etchant/primer compositions). These compositions can be used in methods and kits for improving the bonding of adhesives (and subsequently the adherence of a material, e.g., a dental restorative or an orthodontic appliance) to a hard surface, preferably, to at least one type of medical structure or dental structure. Preferably, compositions of the present invention also function as self-etching adhesives (i.e., etchant/primer/adhesive compositions).

The compositions of the present invention include one or more polymerizable bisphosphonic acids of Formula I, or more particularly, one or more polymerizable bisphosphonic acids of Formula II. Such compounds can be in their acid form (as shown) or in their salt form.

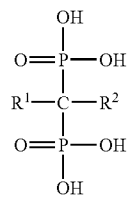

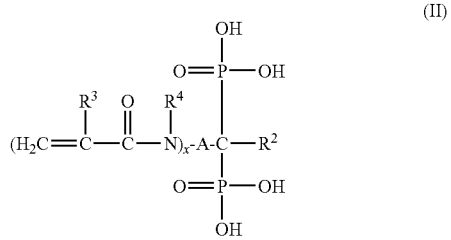

In the compounds of Formula I: $R^1$ is an organic group that includes a polymerizable group; and $R^2$ is H, OR, SR, $N(R)_2$, or an organic group that can optionally join with $R^1$ to form a carbon-carbon double bond with the carbon between the two phosphorus atoms (i.e., the $R^1$ and $R^2$ groups are one and the same with a C=C bond), wherein the organic group optionally includes a polymerizable group, and further wherein each R is independently hydrogen or an organic group optionally including a polymerizable group. In any one compound, the R groups may be the same or different.

In the compounds of Formula II: x=1-3; $R^2$ is H, OH, an alkyl group, an aryl group, an alkoxy group, an aryloxy group, or -A-(N($R^4$)—C(O)—C($R^3$)=$CH_2)_x$; each $R^3$ is independently H or $CH_3$; each $R^4$ is H, an alkyl group, or can be joined to A forming a cyclic organic group; and A is a bond or a straight chain or branched organic group. In any one compound, the groups -A-(N($R^4$)—C(O)—C($R^3$)=$CH_2)_x$ may be the same or different.

Preferably, the polymerizable bisphosphonic acid is present in an amount of at least about 1 percent by weight (wt-%), more preferably, at least about 5 wt-%, based on the total weight of the composition.

For certain preferred embodiments, A of Formula II is a straight chain or branched organic group when the composition includes a polymerizable component that is different from the compound of Formula TI and is otherwise formulated for use as an etchant, more preferably a self-etching primer or a self-etching adhesive, which is particularly useful on hard tissue.

For certain preferred embodiments, A of Formula II is a bond or a straight chain or branched organic group when the composition includes a polymerizable component that is different from the compound of Formula II and the compound of Formula II is present in an amount of at least about 1 wt-%, based on the total weight of the composition.

Certain preferred embodiments of the compositions of the present invention are self-etching primers, thereby being capable of etching and priming a hard surface, particularly a tooth surface, simultaneously. Alternatively, a separate dental primer can be used if desired.

Certain preferred embodiments of the compositions of the present invention are self-etching adhesives, which can, for example, promote adherence of a dental material (e.g., a composite, a filling, a sealant, an inlay, an onlay, a crown, and a bridge) to the tooth surface. Alternatively, a separate dental adhesive can be used if desired.

Certain methods of the present invention involve treating a hard surface that includes etching the hard surface with a composition of the present invention with the proviso that the hard surface is not pretreated.

The compositions of the present invention can function to promote the adherence of an orthodontic adhesive to the tooth surface, wherein the orthodontic adhesive functions to adhere an orthodontic appliance to the tooth surface. Thus, certain methods of the present invention involve adhering an orthodontic appliance (e.g., a bracket, a buccal tube, a band, a cleat, a button, a lingual retainer, and a bite blocker) to the tooth surface after the tooth surface has been etched by a composition including a polymerizable bisphosphonic acid.

In certain preferred methods, an orthodontic adhesive is adhered to the tooth surface, which can optionally be pre-applied to the orthodontic appliance before adhering to the tooth surface. The method can also optionally include a step of priming the tooth surface prior to adhering an orthodontic appliance to the tooth surface. If the composition further includes at least one polymerizable component different from the polymerizable bisphosphonic acid, the steps of etching and priming are done simultaneously with the composition functioning as a self-etching primer composition. The method can also optionally include a step of applying a dental adhesive to the tooth surface prior to adhering an orthodontic appliance to the tooth surface. If the composition further includes at least one polymerizable component different from the polymerizable bisphosphonic acid, the steps of etching and applying a dental adhesive are done simultaneously with the composition acting as a self-etching adhesive composition. For certain embodiments, the methods of the present invention can include adhering an orthodontic adhesive to the tooth surface, wherein preferably the orthodontic adhesive has been pre-applied to the orthodontic appliance before adhering to the tooth surface.

DEFINITIONS

Herein, "adhesive" or "dental adhesive" refers to a composition used as a pre-treatment on a dental structure (e.g., a tooth) to adhere a "dental material" (e.g., "restorative"), an orthodontic appliance (e.g., bracket), or an "orthodontic adhesive" to the dental structure. An "orthodontic adhesive" refers to a highly (generally greater than 40% by weight) filled composition (more analogous to a "restorative material" than to a "dental adhesive") used to adhere an orthodontic appliance to a dental structure (e.g., tooth) surface. Generally, the tooth surface is pre-treated, e.g., by etching, priming, and/or applying an adhesive to enhance the adhesion of the "orthodontic adhesive" to the tooth surface. "Dental structures" refer to tooth structures (e.g., enamel and dentin) and bone, for example.

The terms "comprises" and variations thereof do not have a limiting meaning where these terms appear in the description and claims.

As used herein, "a," "an," "the," "at least one," and "one or more" are used interchangeably.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations.

In each instance, the recited list serves only as a representative group and should not be interpreted as an exclusive list.

DETAILED DESCRIPTION OF ILLUSTRATIVE EMBODIMENTS

The present invention is directed to compositions containing one or more polymerizable bisphosphonic acids. Herein, when bisphosphonic acids are mentioned, this includes the acid form, salts thereof, or combinations thereof. Preferably, the compositions also include one or more additional polymerizable components.

The compositions of the present invention are useful for treating hard surfaces, preferably, hard tissues such as dentin, enamel, and bone. Although the compositions of the present invention are particularly desirable for use on at least one type of medical structure (e.g., bone, cartilage, medical instruments) or dental structure (e.g., dentin, enamel, or bone), they can be used to etch, preferably etch and prime, hard surfaces such as metal and metal oxide surfaces. The compositions of the present invention are typically used with an overlying adhesive (e.g., a dental adhesive), but they can be used as the adhesive (i.e., a self-etching adhesive) in certain preferred embodiments.

Thus, compositions of the present invention are useful as etchants for hard surfaces. In certain preferred embodiments, the compositions are self-etching primers. That is, they can etch and prime a surface in one step, thereby eliminating conventional post-etching rinsing and drying steps. An adhesive is then applied over the etched and primed surface. In certain other preferred embodiments, the compositions are self-etching adhesives. That is, they etch and prime a surface in one step and function as an adhesive.

Such self-etching primer and self-etching adhesive compositions are typically prepared by the addition of one or more polymerizable components to a bisphosphonic acid compound. The selection of additional polymerizable components is made to impart the desired priming and/or adhesive properties to the compositions. Generally, techniques for selecting polymerizable components and optional other components to impart priming and/or adhesive properties to hard-surface treatment compositions are well known to those skilled in formulation of dental and medical materials. Suitable polymerizable components for use in such compositions, as well as conventional dental primers and dental adhesives that can be incorporated into the compositions, or used separately but in combination with the compositions, are discussed herein. Alternatively, priming and/or adhesive properties may be imparted to the composition by chemical modification of the bisphosphonic acid(s) without the addition of other polymerizable components to the composition.

The compositions of the present invention are preferably used to promote the adhesion of a material (e.g., a dental restorative or orthodontic appliance) to a hard surface, particularly a tooth surface (e.g., enamel or dentin). Typically, the compositions are hardened (i.e., polymerized by conventional photopolymerization and/or chemical polymerization techniques) prior to adherence of the material. It is significant if the composition can be formulated to promote adhesion to both enamel and dentin. It is particularly significant if the composition can be formulated to function as the etchant, primer, and adhesive to both enamel and dentin.

The compositions of the present invention can be used to promote the adhesion of dental restoratives (e.g., composites, fillings, sealants, inlays, onlays, crowns, bridges) or orthodontic appliances (e.g., brackets (optionally precoated with orthodontic adhesives), buccal tubes, bands, cleats, buttons, lingual retainers, and bite blockers) to dental structures.

In addition to the polymerizable bisphosphonic acid and other optional polymerizable components, the compositions of the present invention optionally can include fillers, solvents, dental adhesives, and/or dental primers. Various combinations of the components described herein can be used in the compositions of the present invention.

Certain preferred aqueous-based embodiments (i.e., including water in the composition) of the present invention are self-etching primer and self-etching adhesive compositions with enhanced hydrolytic stability, e.g., having a room-temperature shelf-life stability of at least 1 year, and preferably at least 2 years. Additionally, preferred compositions, especially self-etching adhesive compositions, do not require any pre-mixing steps prior to application to the surface of the dental structure.

Bisphosphonic Acids and Salts Thereof

The polymerizable bisphosphonic acids are of the following formula (Formula I):

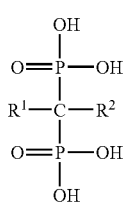
(I)

or a salt thereof, wherein: $R^1$ is an organic group that includes a polymerizable group; and $R^2$ is H, OR, SR, $N(R)_2$, or an organic group that can optionally join with $R^1$ to form a carbon-carbon double bond with the carbon between the two phosphorus atoms, wherein the organic group optionally includes a polymerizable group, and further wherein each R is independently hydrogen or an organic group optionally including a polymerizable group. In the case where $R^1$ and $R^2$ join to form a double bond, that double bond can be the polymerizable group of $R^1$.

Preferably, the polymerizable group is an ethylenically unsaturated group. More preferably, the ethylenically unsaturated group is a (meth)acrylate group, a (meth)acrylamido group, or a vinyl group.

A particularly preferred class of polymerizable bisphosphonic acids is of the following formula (Formula II):

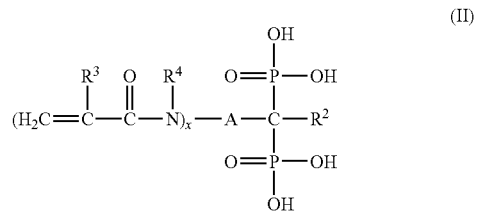
(II)

or a salt thereof, wherein: x=1-3 (preferably, x is 1-2, and more preferably, 1); $R^2$ is H, OH, an alkyl group, an aryl group, an alkoxy group, an aryloxy group, or -A-(N($R^4$)C(O)C($R^3$)=$CH_2)_x$; each $R^3$ is independently H or $CH_3$ (i.e, an acrylamido group or a methacrylamido group, often referred to as a (meth)acrylamido group); each $R^4$ is independently H, an alkyl group, or can be joined to A forming a cyclic organic group; and A is a bond or a straight chain or branched organic group. When x is 2 or 3, preferably, the ethylenically unsaturated groups (x) are not bonded to the same carbon atom of A. They can be present in their acid form or their salt form. Thus, when a compound of Formulas I or II or other bisphosphonic acids of the present invention are referred to herein, they encompass both acids and salts.

Preferably, a polymerizable bisphosphonic acid compound of the present invention is present in a composition in an amount effective to etch hard tissue. Typically, this is an amount of at least about 1 percent by weight (wt-%), based on the total weight of the composition. More preferably, a polymerizable bisphosphonic acid compound of the present invention is present in an amount of at least about 5 wt-%, based on the total weight of the composition. If more than one polymerizable bisphosphonic acid compound is used, these amounts apply to the total amount of the mixture.

In the formulas for the bisphosphonic acid compounds described herein, the term "organic group" means a hydrocarbon group (with optional elements other than carbon and hydrogen, such as oxygen, nitrogen, sulfur, phosphorus, and silicon) that is classified as an aliphatic group, cyclic group, or combination of aliphatic and cyclic groups (e.g., alkaryl and aralkyl groups). In the context of the present invention, the organic groups are those that do not interfere with the formation of an etchant for a hard surface. The term "aliphatic group" means a saturated or unsaturated linear or branched hydrocarbon group. This term is used to encompass alkyl, alkenyl, and alkynyl groups, for example. The term "alkyl group" means a saturated linear or branched hydrocarbon group including, for example, methyl, ethyl, isopropyl, t-butyl, heptyl, dodecyl, octadecyl, amyl, 2-ethylhexyl, and the like. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polynuclear aromatic hydrocarbon group. The term "heterocyclic group" means a closed ring hydrocarbon in which one or more of the atoms in the ring is an element other than carbon (e.g., nitrogen, oxygen, sulfur, etc.).

Substitution is anticipated on the organic groups of the polymerizable bisphosphonic acid compounds of the present invention. As a means of simplifying the discussion and recitation of certain terminology used throughout this application, the terms "group" and "moiety" are used to differentiate between chemical species that allow for substitution or that may be substituted and those that do not allow or may not be so substituted. Thus, when the term "group" is used to describe a chemical substituent, the described chemical material includes the unsubstituted group and that group with O, N, Si, P, or S atoms, for example, in the chain (as in an alkoxy group) as well as carbonyl groups or other conventional substitution. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, t-butyl, and the like.

For certain embodiments of R, $R^1$, $R^2$, and A, the organic groups can include up to 20 carbon atoms (preferably, up to 18 carbon atoms, and more preferably up to 12 carbon atoms).

For certain embodiments of R, $R^1$, and $R^2$, the organic group can include a polymerizable group. Examples of such polymerizable groups include, for example, (meth)acrylamido groups, (meth)acryloxy groups, and vinyl groups. Preferably, the polymerizable groups are (meth)acrylamido groups.

For certain embodiments of $R^2$, the alkyl and alkoxy groups have 1-18 carbon atoms (preferably, 1-8 carbon atoms, and more preferably 1-4 carbon atoms), and the aryl and aryloxy groups have 4-18 carbon atoms (preferably, 5-12 carbon atoms, and more preferably 6-10 carbon atoms). For certain embodiments of the present invention, $R^2$ is H, OH, (C1-C4)alkyl group, or a (C1-C4)alkoxy group. For certain embodiments, $R^2$ is OH or a (C1-C4)alkoxy group. For certain embodiments, $R^2$ is H, OH, methyl, or methoxy.

For certain embodiments of $R^4$, the alkyl group has 1-18 carbon atoms (preferably, 1-8 carbon atoms, and more preferably 1-4 carbon atoms). For certain embodiments of the present invention, $R^4$ is H, a (C1-C4)alkyl group, or can be joined to A forming a cyclic organic group. For more preferred embodiments, $R^4$ is H or methyl.

For certain embodiments of the present invention, A is a straight chain alkyl group, preferably having up to 20 carbon atoms. For more preferred embodiments, A is $(CH_2)_n$ wherein n=1-20. For even more preferred embodiments, A is $(CH_2)_n$ wherein n=3-11. For even more preferred embodiments, n=5.

Polymerizable Components

The compositions of the present invention, especially self-etching primer and self-etching adhesive compositions, can also include one or more polymerizable components in addition to the polymerizable bisphosphonic acid, thereby forming polymerizable compositions.

In certain embodiments, the compositions are photopolymerizable, i.e., the compositions contain a photopolymerizable component and a photoinitiator (i.e., a photoinitiator system) that upon irradiation with actinic radiation initiates the polymerization (or hardening) of the composition. Such photopolymerizable compositions can be free radically polymerizable.

In certain embodiments, the compositions are chemically polymerizable, i.e., the compositions contain a chemically polymerizable component and a chemical initiator (i.e., initiator system) that can polymerize, cure, or otherwise harden the composition without dependence on irradiation with actinic radiation. Such chemically polymerizable compositions are sometimes referred to as "self-cure" compositions and may include glass ionomer cements, resin-modified glass ionomer cements, redox cure systems, and combinations thereof.

Photopolymerizable Compositions

Suitable photopolymerizable compositions may include photopolymerizable components (e.g., compounds) that include ethylenically unsaturated compounds (which contain free radically active unsaturated groups). Examples of useful ethylenically unsaturated compounds include acrylic acid esters, methacrylic acid esters, hydroxy-functional acrylic acid esters, hydroxy-functional methacrylic acid esters, and combinations thereof.

Photopolymerizable compositions may include compounds having free radically active functional groups that may include monomers, oligomers, and polymers having one or more ethylenically unsaturated groups. Suitable compounds contain at least one ethylenically unsaturated bond and are capable of undergoing addition polymerization. Such free radically polymerizable compounds include mono-, di- or poly-(meth)acrylates (i.e., acrylates and methacrylates) such as, methyl (meth)acrylate, ethyl (meth)acrylate, isopropyl (meth)acrylate, n-hexyl (meth)acrylate, stearyl (meth)acrylate, allyl (meth)acrylate, glycerol tri(meth)acrylate, ethyleneglycol di(meth)acrylate, diethyleneglycol di(meth)acrylate, triethyleneglycol di(meth)acrylate, 1,3-propanediol di(meth)acrylate, trimethylolpropane tri(meth)acrylate, 1,2,4-butanetriol tri(meth)acrylate, 1,4-cyclohexanediol di(meth)acrylate, pentaerythritol tetra(meth)acrylate, sorbitol hex(meth)acrylate, tetrahydrofurfuryl(meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenolA di(meth)acrylate, and trishydroxyethyl-isocyanurate tri(meth)acrylate; (meth)acrylamides (i.e., acrylamides and methacrylamides) such as (meth)acrylamide, methylene bis-(meth)acrylamide, and diacetone (meth)acrylamide; urethane (meth)acrylates; the bis-(meth)acrylates of polyethylene glycols (preferably of molecular weight 200-500), copolymerizable mixtures of acrylated monomers such as those in U.S. Pat. No. 4,652,274 (Boettcher et al.), and acrylated oligomers such as those of U.S. Pat. No. 4,642,126 (Zador et al.); and vinyl compounds such as styrene, diallyl phthalate, divinyl succinate, divinyl adipate and divinyl phthalate. Other suitable free radically polymerizable compounds include siloxane-functional (meth)acrylates as disclosed, for example, in WO-00/38619 (Guggenberger et al.), WO-01/92271 (Weinmann et al.), WO-01/07444 (Guggenberger et al.), WO-00/42092 (Guggenberger et al.) and fluoropolymer-functional (meth)acrylates as disclosed, for example, in U.S. Pat. No. 5,076,844 (Fock et al.), U.S. Pat. No. 4,356,296 (Griffith et al.), EP-0373 384 (Wagenknecht et al.), EP-0201 031 (Reiners et al.), and EP-0201 778 (Reiners et al.). Mixtures of two or more free radically polymerizable compounds can be used if desired.

The polymerizable component may also contain hydroxyl groups and free radically active functional groups in a single molecule. Examples of such materials include hydroxyalkyl (meth)acrylates, such as 2-hydroxyethyl (meth)acrylate and 2-hydroxypropyl (meth)acrylate; glycerol mono- or di-(meth)acrylate; trimethylolpropane mono- or di-(meth)acrylate; pentaerythritol mono-, di-, and tri-(meth)acrylate; sorbitol mono-, di-, tri-, tetra-, or penta-(meth)acrylate; and 2,2-bis[4-(2-hydroxy-3-methacryloxypropoxy)phenyl]propane (bisGMA). Suitable ethylenically unsaturated compounds are also available from a wide variety of commercial sources, such as Sigma-Aldrich, St. Louis, Mo. and Rhom and Tech, Inc., Darmstadt, Germany. Mixtures of ethylenically unsaturated compounds can be used if desired.

The polymerizable component may also be an ethylenically unsaturated compound with acid functionality. As used herein, ethylenically unsaturated compounds with acid functionality is meant to include monomers, oligomers, and polymers having ethylenic unsaturation and acid and/or acid-precursor functionality. Acid-precursor functionalities include, for example, anhydrides, acid halides, and pyrophosphates. Such ethylenically unsaturated compounds with acid functionality are present in certain embodiments of the present invention.

Exemplary ethylenically unsaturated compounds with acid functionality include, for example, $\alpha,\beta$-unsaturated acidic compounds such as glycerol phosphate mono(meth)acrylates, glycerol phosphate di(meth)acrylates, hydroxyethyl (meth)acrylate phosphates, citric acid mono-, di-, and tri-(meth)acrylates, poly(meth)acrylated oligomaleic acid, poly (meth)acrylated polymaleic acid, poly(meth)acrylated poly (meth)acrylic acid, poly(meth)acrylated polycarboxyl-polyphosphonic acid, poly(meth)acrylated polychlorophosphoric acid, poly(meth)acrylated polysulfonate, poly(meth)acrylated polyboric acid, and the like. Suitable compositions of the present invention include an ethylenically unsaturated compound with acid functionality having at least one P—OH moiety.

Certain of these compounds are obtained, for example, as reaction products between isocyanatoalkyl(meth)acrylates and carboxylic acids (e.g., the bis-isocyanatoethylmethacrylate derivative of bis-hydroxymethylpropionic acid (PDMA) or the bis-isocyanatoethylmethacrylate derivative of citric acid (CDMA)). Additional compounds of this type having both acid-functional and ethylenically unsaturated components are described in U.S. Pat. Nos. 4,872,936 (Engelbrecht) and 5,130,347 (Mitra). A wide variety of such compounds containing both the ethylenically unsaturated and acid moieties can be used. Mixtures of such compounds can be used if desired.

Additional ethylenically unsaturated compounds with acid functionality include, for example, AA:ITA:IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, for example, in Example 11 of U.S. Pat. No. 5,130,347 (Mitra)); and those recited in U.S. Pat. Nos. 4,259,075 (Yamauchi et al.), 4,499,251 (Omura et al.), 4,537,940 (Omura et al.), 4,539,382 (Omura et al.), 5,530,038 (Yamamoto et al.), 6,458,868 (Okada et al.), and European Pat. Application Publication Nos. EP 712,622 (Tokuyama Corp.) and EP 1,051, 961 (Kuraray Co., Ltd.). Further, the combination of an ethylenically unsaturated phosphorylated compound and a carboxylic acid functional polymer are disclosed, for example, in U.S. Pat. No. 5,256,447 (Oxman et al.).

Preferred photopolymerizable components include 2-hydroxyethyl methacrylate (HEMA), PEGDMA (polyethyleneglycol dimethacrylate having a molecular weight of about 400), AA:ITA:IEM (copolymer of acrylic acid:itaconic acid with pendent methacrylate as described in the Examples Section), bisGMA, UDMA (urethane dimethacrylate), and GDMA (glycerol dimethacrylate).

Various combinations of the polymerizable components can be used if desired.

Suitable photoinitiators (i.e., photoinitiator systems that include one or more compounds) for polymerizing free radically photopolymerizable compositions include binary and tertiary systems. Typical binary photoinitiators include a photosensitizer and an electron donor compound. Typical tertiary photoinitiators include an iodonium salt, a photosensitizer, and an electron donor compound as described in U.S. Pat. No. 5,545,676 (Palazzotto et al.). Preferred iodonium salts are the diaryl iodonium salts, e.g., diphenyliodonium chloride, diphenyliodonium hexafluorophosphate, and diphenyliodonium tetrafluoroboarate. Preferred photosensitizers are monoketones and diketones that absorb some light within a range of about 450 nm to about 520 nm (preferably, about 450 nm to about 500 nm).

Exemplary alpha-diketones include 2,3-butanedione, 2,3-pentanedione, 2,3-hexanedione, 3,4-hexanedione, 2,3-heptanedione, 3,4-heptanedione, 2,3-octanedione, 4,5-octanedione, benzil, 2,2'-, 3,3'-, and 4,4'-dihydroxybenzil, furil, di-3, 3'-indolylethanedione, 2,3-bornanedione (camphorquinone), biacetyl, 1,2-cyclohexanedione, 3,3,6,6-tetramethylcyclohexanedione, 1,2-naphthaquinone, acenaphthaquinone, and the like. Additional diketones include 1-aryl-2-alkyl-1,2-ethanediones such as 1-phenyl-1,2-propanedione, as disclosed, for example, in U.S. Pat. No. 6,204,302 (Rawls et al.). More preferred compounds are alpha diketones that have some light absorption within a range of about 450 nm to about 520 nm (even more preferably, about 450 to about 500 nm). Preferred compounds are camphorquinone, benzil, furil, 3,3, 6,6-tetramethylcyclohexanedione, phenanthraquinone and other cyclic alpha diketones. Most preferred is camphorquinone.

Preferred electron donor compounds include substituted amines, e.g., ethyl dimethylaminobenzoate.

Other suitable photoinitiators for polymerizing free radically photopolymerizable compositions include the class of phosphine oxides that typically have a functional wavelength range of about 380 nm to about 1200 nm. Preferred phosphine oxide free radical initiators with a functional wavelength range of about 380 nm to about 450 nm are acyl and bisacyl phosphine oxides such as those described in U.S. Pat. Nos. 4,298,738 (Lechtken et al.), 4,324,744 (Lechtken et al.), 4,385,109 (Lechtken et al.), 4,710,523 (Lechtken et al.), and 4,737,593 (Ellrich et al.), 6,251,963 (Kohler et al.); and EP Application No. 0 173 567 A2 (Ying).

Commercially available phosphine oxide photoinitiators capable of free-radical initiation when irradiated at wavelength ranges of greater than about 380 nm to about 450 nm include bis(2,4,6-trimethylbenzoyl)phenyl phosphine oxide (IRGACURE 819, Ciba Specialty Chemicals, Tarrytown, N.Y.), bis(2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2, 4,4-trimethylpentyl phosphine oxide and 2-hydroxy-2-methyl-1-phenylpropan-1-one (IRGACURE 1700, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Typically, the phosphine oxide initiator is present in the photopolymerizable composition in catalytically effective amounts, such as from about 0.1 weight percent to about 5.0 weight percent, based on the total weight of the composition.

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate. When present, the amine reducing agent is present in the photopolymerizable composition in an amount from about 0.1 weight percent to about 5.0 weight percent, based on the total weight of the composition.

Chemically Polymerizable Compositions

The chemically polymerizable compositions may include glass ionomer cements such as conventional glass ionomers that typically employ as their main ingredients a homopolymer or copolymer of an ethylenically unsaturated carboxylic acid (e.g., poly(acrylic acid), copoly(acrylic, itaconic acid), copoly(acrylic, maleic acid), and the like), a fluoroaluminosilicate ("FAS") glass, water, and a chelating agent such as tartaric acid. Conventional glass ionomers (i.e., glass ionomer cements) typically are supplied in powder/liquid formulations that are mixed just before use. The mixture will undergo self-hardening in the dark due to an ionic reaction between the acidic repeating units of the polycarboxylic acid and cations leached from the glass.

The glass ionomer cements may include resin-modified glass ionomer ("RMGI") cements. Like a conventional glass ionomer, an RMGI cement employs an FAS glass. However, the organic portion of an RMGI is different. In one type of RMGI, the polycarboxylic acid is modified to replace or end-cap some of the acidic repeating units with pendent curable groups and a photoinitiator is added to provide a second cure mechanism, e.g., as described in U.S. Pat. No. 5,130,347 (Mitra). Acrylate or methacrylate groups are usually employed as the pendant curable group. In another type of RMGI, the cement includes a polycarboxylic acid, an acrylate or methacrylate-functional monomer and a photoinitiator, e.g., as in Mathis et al., "Properties of a New Glass Tonomer/Composite Resin Hybrid Restorative," Abstract No. 51, J. Dent Res., 66:113 (1987) and as in U.S. Pat. Nos. 5,063,257 (Akahane et al.), 5,520,725 (Kato et al.), 5,859,089 (Qian), 5,925,715 (Mitra) and 5,962,550 (Akahane et al.). In another type of RMGI, the cement may include a polycarboxylic acid, an acrylate or methacrylate-functional monomer, and a redox or other chemical cure system, e.g., as described in U.S. Pat. Nos. 5,154,762 (Mitra et al.), 5,520,725 (Kato et al.), and 5,871,360 (Kato). In another type of RMGI, the cement may include various monomer-containing or resin-containing components as described in U.S. Pat. Nos. 4,872,936 (Engelbrecht), 5,227,413 (Mitra), 5,367,002 (Huang et al.), and 5,965,632 (Orlowski). RMGI cements are preferably formulated as powder/liquid or paste/paste systems, and contain water as mixed and applied. The compositions are able to harden in the dark due to the ionic reaction between the acidic repeating units of the polycarboxylic acid and cations leached from the glass, and commercial RMGI products typically also cure on exposure of the cement to light from a dental curing lamp. RMGI cements that contain a redox cure system and that can be cured in the dark without the use of actinic radiation are described in U.S. Patent Publication No. 2003/0087986 (Filed Jul. 27, 2001).

The chemically polymerizable compositions may include redox cure systems that include a polymerizable component (e.g., an ethylenically unsaturated polymerizable component) and redox agents that include an oxidizing agent and a reducing agent. Suitable polymerizable components, redox agents, optional acid-functional components, and optional fillers that are useful in the present invention are described in U.S. Patent Publication No. 2003/0166740 (Filed Apr. 12, 2002) and U.S. Patent Publication No. 2003/0195273 (Filed Apr. 12, 2002).

The reducing and oxidizing agents should react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical dental conditions. They should be sufficiently miscible with the resin system (and preferably water-soluble) to permit ready dissolution in (and discourage separation from) the other components of the polymerizable composition.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. In some embodiments it may be preferred to include a secondary ionic salt to enhance the stability of the polymerizable composition as described in U.S. Patent Publication No. 2003/0195273 (Filed Apr. 12, 2002).

The reducing and oxidizing agents are present in amounts sufficient to permit an adequate free-radical reaction rate. This can be evaluated by combining all of the ingredients of the polymerizable composition except for the optional filler, and observing whether or not a hardened mass is obtained.

Preferably, a reducing agent is present in an amount of at least about 0.01 wt-%, and more preferably at least about 0.1 wt-%, based on the total weight (including water) of the components of the polymerizable composition. Preferably, a reducing agent is present in an amount of no greater than about 10 wt-%, and more preferably no greater than about 5 wt-%, based on the total weight (including water) of the components of the polymerizable composition.

Preferably, an oxidizing agent is present in an amount of at least about 0.01 wt-%, and more preferably at least about 0.10 wt-%, based on the total weight (including water) of the components of the polymerizable composition. Preferably, an oxidizing agent is present in an amount of no greater than about 10 wt-%, and more preferably no greater than about 5 wt-%, based on the total weight (including water) of the components of the polymerizable composition.

The reducing or oxidizing agents can be microencapsulated as described in U.S. Pat. No. 5,154,762 (Mitra et al.).

This will generally enhance shelf stability of the polymerizable composition, and if necessary permit packaging the reducing and oxidizing agents together. For example, through appropriate selection of an encapsulant, the oxidizing and reducing agents can be combined with an acid-functional component and optional filler and kept in a storage-stable state. Likewise, through appropriate selection of a water-insoluble encapsulant, the reducing and oxidizing agents can be combined with an FAS glass and water and maintained in a storage-stable state.

A redox cure system can be combined with other cure systems, e.g., with a glass ionomer cement and with a photopolymerizable composition such as described U.S. Pat. No. 5,154,762 (Mitra et al.).

The polymerizable compositions that utilize a redox cure system can be supplied in a variety of forms including two-part powder/liquid, paste/liquid, and paste/paste systems. Other forms employing multi-part combinations (i.e., combinations of two or more parts), each of which is in the form of a powder, liquid, gel, or paste are also possible. In a multi-part system, one part typically contains the reducing agent(s) and another part typically contains the oxidizing agent(s). Therefore, if the reducing agent is present in one part of the system, then the oxidizing agent is typically present in another part of the system. However, the reducing agent and oxidizing agent can be combined in the same part of the system through the use of the microencapsulation technique.

Optional Fillers

The compositions of the present invention can also contain fillers. Fillers may be selected from one or more of a wide variety of materials suitable for incorporation in compositions used for dental applications, such as fillers currently used in dental restorative compositions, and the like.

The filler is preferably finely divided. The filler can have a unimodial or polymodial (e.g., bimodal) particle size distribution. Preferably, the maximum particle size (the largest dimension of a particle, typically, the diameter) of the filler is less than about 10 micrometers, and more preferably less than about 2.0 micrometers. Preferably, the average particle size of the filler is less than about 3.0 micrometers, and more preferably less than about 0.6 micrometer.

The filler can be an inorganic material. It can also be a crosslinked organic material that is insoluble in the resin system, and is optionally filled with inorganic filler. The filler should in any event be nontoxic and suitable for use in the mouth. The filler can be radiopaque or radiolucent. The filler typically is substantially insoluble in water.

Examples of suitable inorganic fillers are naturally occurring or synthetic materials including, but not limited to: quartz; nitrides (e.g., silicon nitride); glasses derived from, for example, Ce, Sb, Sn, Ba, Zn, and Al; feldspar; borosilicate glass; kaolin; talc; titania; low Mohs hardness fillers such as those described in U.S. Pat. No. 4,695,251 (Randklev); and submicron silica particles (e.g., pyrogenic silicas such as those available under the trade designations AEROSIL, including "OX 50," "130," "150" and "200" silicas from Degussa Corp., Akron, Ohio and CAB-O-SIL M5 silica from Cabot Corp., Tuscola, Ill.). Examples of suitable organic filler particles include filled or unfilled pulverized polycarbonates, polyepoxides, and the like.

Preferred non-acid-reactive filler particles are quartz, submicron silica, and non-vitreous microparticles of the type described in U.S. Pat. No. 4,503,169 (Randklev). Mixtures of these non-acid-reactive fillers are also contemplated, as well as combination fillers made from organic and inorganic materials.

The surface of the filler particles can also be treated with a coupling agent in order to enhance the bond between the filler and the resin. The use of suitable coupling agents include gamma-methacryloxypropyltrimethoxysilane, gamma-mercaptopropyltriethoxysilane, gamma-aminopropyltrimethoxysilane, and the like.

The filler can also be an acid-reactive filler. An acid-reactive filler is typically used in combination with an acid-functional resin component, and may or may not be used in combination with a nonreactive filler. The acid-reactive filler can, if desired, also possess the property of releasing fluoride. Suitable acid-reactive fillers include metal oxides, glasses, and metal salts. Preferred metal oxides include barium oxide, calcium oxide, magnesium oxide, and zinc oxide. Preferred glasses include borate glasses, phosphate glasses, and fluoroaluminosilicate ("FAS") glasses. FAS glasses are particularly preferred. The FAS glass preferably contains sufficient elutable cations so that a hardened dental composition will form when the glass is mixed with the components of the hardenable composition. The glass also preferably contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass preferably is in the form of particles that are sufficiently finely divided so that they can conveniently be mixed with the other cement components and will perform well when the resulting mixture is used in the mouth.

Preferably, the average particle size (typically, diameter) for the FAS glass is no greater than about 10 micrometers, and more preferably no greater than about 5 micrometers as measured using, for example, a sedimentation analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT and KETAC-FIL (3M ESPE Dental Products, St. Paul, Minn.), FUJI II, GC FUJI LC and FUJI IX (G-C Dental Industrial Corp., Tokyo, Japan) and CHEMFIL Superior (Dentsply International, York, Pa.). Mixtures of fillers can be used if desired.

The FAS glass can optionally be subjected to a surface treatment. Suitable surface treatments include, but are not limited to, acid washing (e.g., treatment with a phosphoric acid), treatment with a phosphate, treatment with a chelating agent such as tartaric acid, and treatment with a silane or an acidic or basic silanol solution. Desirably the pH of the treating solution or the treated glass is adjusted to neutral or near-neutral, as this can increase storage stability of the hardenable composition.

In certain compositions mixtures of acid-reactive and non-acid-reactive fillers can be used either in the same part or in different parts.

Other suitable fillers are disclosed in U.S. Pat. No. 6,387,981 (Zhang et al.) as well as International Publication Nos. WO 01/30304 (Wu et al.), WO 01/30305 (Zhang et al.), WO 01/30306 (Windisch et al.), and WO 01/30307 (Zhang et al.).

U.S. Pat. No. 6,306,926 (Bretscher et al.) discloses a number of radiopacifying fillers that can be used in both free radically polymerizable compositions, cationically polymerizable compositions, and hybrid compositions featuring both free radically and cationically polymerizable components. They are particularly advantageous for use in cationically polymerizable compositions. One such filler is a melt-derived filler that includes 5-25% by weight aluminum oxide, 10-35% by weight boron oxide, 15-50% by weight lanthanum oxide, and 20-50% by weight silicon oxide. Another filler is a melt-derived filler that includes 10-30% by weight aluminum oxide, 10-40% by weight boron oxide, 20-50% by weight silicon oxide, and 15-40% by weight tantalum oxide. A third filler is a melt-derived filler that includes 5-30% by weight aluminum oxide, 5-40% by weight boron oxide, 0-15% by weight lanthanum oxide, 25-55% by weight silicon oxide, and 10-40% by weight zinc oxide. A fourth filler is a melt-derived filler that includes 15-30% by weight aluminum oxide, 15-30% by weight boron oxide, 20-50% by weight silicon oxide, and 15-40% by weight ytterbium oxide. A fifth filler is in the form of non-vitreous microparticles prepared by a sol-gel method in which an aqueous or organic dispersion or sol of amorphous silicon oxide is mixed with an aqueous or organic dispersion, sol, or solution of a radiopacifying metal oxide, or precursor organic or compound. A sixth filler is in the form of non-vitreous microparticles prepared by a sol-gel method in which an aqueous or organic dispersion or sol of amorphous silicon oxide is mixed with an aqueous or organic dispersion, sol, or solution of a radiopacifying metal oxide, or precursor organic or inorganic compound.

Optional Photobleachable Dye

In some embodiments, compositions of the present invention preferably have an initial color remarkably different than dental structures. Color is preferably imparted to a composition through the use of a photobleachable dye. A composition of the present invention preferably includes at least 0.001% by weight photobleachable dye, and more preferably at least 0.002% by weight photobleachable dye, based on the total weight of the composition. A composition of the present invention preferably includes at most 1% by weight photobleachable dye, and more preferably at most 0.1% by weight photobleachable dye, based on the total weight of the composition. The amount of photobleachable dye may vary depending on its extinction coefficient, the ability of the human eye to discern the initial color, and the desired color change.

The color formation and bleaching characteristics of the photobleachable dye varies depending on a variety of factors including, for example, acid strength, dielectric constant, polarity, amount of oxygen, and moisture content in the atmosphere. However, the bleaching properties of the dye can be readily determined by irradiating the composition and evaluating the change in color. Preferably, at least one photobleachable dye is at least partially soluble in a hardenable resin.

Exemplary classes of photobleachable dyes are disclosed, for example, in U.S. Pat. Nos. 6,331,080 (Cole et al.), U.S. Pat. No. 6,444,725 (Trom et al.), and 6,528,555 (Nikutowski et al.). Preferred dyes include, for example, Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein, and combinations thereof.

The color change in the inventive compositions is initiated by light. Preferably, the composition's color change is initiated using actinic radiation using, for example, a dental curing light which emits visible or near infrared (IR) light for a sufficient amount of time. The mechanism that initiates the color change in the compositions of the invention may be separate from or substantially simultaneous with the hardening mechanism that hardens the resin. For example, a composition may harden when polymerization is initiated chemically (e.g., redox initiation) or thermally, and the color change from an initial color to a final color may occur subsequent to the hardening process upon exposure to actinic radiation.

The change in composition color from an initial color to a final color is preferably quantified by a Color Test as described below. Using the Color Test, a value of $\Delta E^*$ is determined, which indicates the total color change in a 3-dimensional color space. The human eye can detect a color change of approximately 3 $\Delta E^*$ units in normal lighting conditions. The dental compositions of the present invention are preferably capable of having a color change, $\Delta E^*$, of at least 20; more preferably, $\Delta E^*$ is at least 30; most preferably $\Delta E^*$ is at least 40.

Optional Additives

Optionally, the polymerizable compositions also may contain solvents or diluents (e.g., water, alcohols (e.g., propanol, ethanol), ketones (e.g., acetone, methyl ethyl ketone), and other nonaqueous solvents (e.g., dimethylformamide, dimethylacetamide, dimethylsulfoxide, 1-methyl-2-pyrrolidinone)). If desired, the compositions of the invention can contain additives such as pigments, inhibitors, accelerators, viscosity modifiers, surfactants, fluoride releasing agents, and other ingredients that will be apparent to those skilled in the art.

Suitable fluoride releasing agents include fluoride salts as disclosed, for example, in U.S. Pat. Nos. 5,607,663 (Rozzi et al.), U.S. Pat. No. 5,662,887 (Rozzi et al.), U.S. Pat. No. 5,866,630 (Mitra et al.), U.S. Pat. No. 5,876,208 (Mitra et al.), U.S. Pat. No. 5,888,491 (Mitra et al.), and U.S. Pat. No. 6,312,668 (Mitra et al.). A preferred fluoride releasing agent includes tetrafluoroborate anions as disclosed, for example, in U.S. Pat. No. 4,871,786 (Aasen et al.). A preferred repeating unit of a fluoride releasing agent includes trimethylammoniumethyl methacrylate.

Dental Primers

Numerous examples of hard tissue dental primers are known, which can be used as a component of compositions of the present invention or as a separate primer used in conjunction with compositions of the present invention. For example, U.S. Pat. Nos. 5,554,030 (Ario et al.) and U.S. Pat. No. 5,525,648 (Aasen et al.) include a variety of materials and methods for applying a priming solution containing a film-former to an etched dental surface. Such materials and methods are described as part of an overall sequence of method steps for bonding dental restorative materials to a dental surface. Examples of commercially available dental primers include SCOTCHBOND MULTI-PURPOSE Primer available from 3M ESPE Dental, St. Paul, Minn. and CLEARFIL SE (self-etching primer) available from Kuraray Company, Japan.

Dental Adhesives

Numerous examples of hard tissue adhesives are known, which can be used as a component of compositions of the present invention or as a separate adhesive used in conjunction with compositions of the present invention. For example, U.S. Pat. No. 4,719,149 (Aasen et al.) and references therein include a variety of materials and methods for adhering methacrylate-based composites to hard tissues. There are many other patents that describe various preferred materials and protocols for bonding to teeth, such as for example, U.S. Pat. Nos. 5,256,447 (Oxman et al.) and U.S. Pat. No. 5,525,648 (Aasen et al.). U.S. Pat. No. 5,980,253 (Oxman et al.) describes materials and methods for bonding cationically curable compositions to hard tissues.

Such known materials and methods can be used in the processes of the present invention. Generally, these materials have been used in processes that initially harden the adhesive and then the restorative material. That is, conventional methods utilize one or more of the following steps: surface treatment of the tooth (e.g., etching, priming), application of a hardenable adhesive to the primed tooth surface, curing of the adhesive, placement of a restorative material on the hardened adhesive, and curing of the restorative material. Examples of commercially available dental adhesives and adhesive systems include SCOTCHBOND MULTI-PURPOSE adhesive, SINGLEBOND adhesive (self-priming adhesive), and ADPER PROMPT L-POP (self-etching adhesive) all available from 3M ESPE Dental, St. Paul, Minn.

Methods and Kits

A composition of the present invention is applied to a hard surface, typically a dental structure requiring restoration, for a time sufficient to etch, and preferably etch and prime, the surface, using conventional techniques. Thereafter, optionally, the applied composition may be rinsed, dried, or both. More preferably, a composition of the present invention is a self-etching adhesive that requires only a single application. Specific techniques are described in greater detail in the Examples Section.

Certain methods of the present invention involve adhering an orthodontic appliance (e.g., a bracket, a buccal tube, a band, a cleat, a button, a lingual retainer, and a bite blocker) to the tooth surface after the tooth surface has been etched by a composition including a polymerizable bisphosphonic acid. In such embodiments, an orthodontic adhesive can be adhered to the tooth surface, which can optionally be pre-applied to the orthodontic appliance before adhering to the tooth surface.

In the case of utilizing an orthodontic adhesive to adhere an orthodontic appliance to a tooth surface, the following steps have traditionally been used to prepare the tooth surface: etchant application (typically a phosphoric acid solution), rinse, dry, primer application, dry, orthodontic adhesive application. By using an etching composition of the present invention (containing a polymerizable bisphosphonic acid compound of the present invention), it should be possible to eliminate, at a minimum, the rinsing step of the traditional process; and additionally eliminate the bitter aftertaste that patients experience from the use of phosphoric acid. By using self-etching primer or self-etching adhesive compositions of the present invention, additional steps of the traditional process can be eliminated as previously discussed herein.

For example, if the composition further includes at least one polymerizable component different from the polymerizable bisphosphonic acid, steps of etching and priming are done simultaneously with the composition functioning as a self-etching primer composition. Alternatively, if the composition further includes at least one polymerizable component different from the polymerizable bisphosphonic acid, steps of etching and applying a dental adhesive are done simultaneously with the composition acting as a self-etching adhesive composition. For certain embodiments, the methods of the present invention can include adhering an orthodontic adhesive to the tooth surface, wherein preferably the orthodontic adhesive has been pre-applied to the orthodontic appliance before adhering to the tooth surface.

For embodiments in which the composition functions only as a self-etching primer, an adhesive is subsequently applied to the primed hard surface. Typically, the adhesive contains an initiator and either immediately before or immediately after application of the adhesive, curing is initiated to form a polymeric structure on the hard surface.

The components of the compositions can be used in kit form with various containers. For example, an etchant composition can be packaged along with separate containers of dental primers and dental adhesives or along with a separate container of a self-priming adhesive. Alternatively, a self-etching primer composition can be packaged along with a separate container of adhesive. As other embodiments, a self-etching adhesive composition could be packaged as a two-part system requiring mixing immediately prior to application and/or could be packaged along with a suitable applicator.

EXAMPLES

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis, all water is deionized water, and all molecular weights are weight average molecular weight.

Test Methods

Shear Bond Strength to Enamel and Dentin Test

Preparation of Teeth. Bovine incisal teeth, free of soft tissue, were embedded in circular acrylic disks. The embedded teeth were stored in water in a refrigerator prior to use. In preparation for adhesive testing, the embedded teeth were ground to expose a flat enamel or dentin surface using 120-grit sandpaper mounted on a lapidary wheel. Further grinding and polishing of the tooth surface was done using 320-grit sandpaper on the lapidary wheel. The teeth were continuously rinsed with water during the grinding process.

Teeth Treatment. A test sample was applied with a dental applicator brush over the entire surface of the prepared enamel or dentin surface and allowed to stand on the tooth surface for about 20 seconds. The coating was then thinned using a gentle to moderate stream of air for about 1-2 seconds. Using a clean application brush, an overcoat adhesive layer was optionally applied on top of the sample layer. The adhesive materials utilized are shown in Table 1. The overcoat adhesive layer was air thinned with a gentle stream of air for about 1-2 seconds and then light cured for 10 seconds. A 2.5-mm thick Teflon mold with a hole approximately 4.7 mm in diameter was clamped to the embedded tooth such that the hole in the mold exposed part of the adhesively prepared tooth surface. A composite material, FILTEK Z250 Universal Restorative (3M Company, St. Paul, Minn.), was filled into the hole such that the hole was completely filled, but not overfilled, and light cured per manufacturer's instructions to form a "button" that was adhesively attached to the tooth.

Shear Bond Strength Testing. The molds were carefully removed from the embedded teeth, leaving the button of FILTEK Z250 composite attached to each tooth surface. One at a time, the samples were mounted in an INSTRON machine such that the tooth surface was parallel to the direction of the pulling shear force. A loop of wire (0.75-mm thick) was placed around the button flush with the tooth surface, and the pulling shear force was started at a crosshead speed of 2 mm/minute. The force in kilograms (kg) at which the bond failed was recorded, and this number was converted to a force per unit area (units of $kg/cm^2$ or MPa) using the known surface area of the button. Each reported value represents the average of 5 replicates.

| Abbreviations/Definitions | |
|---|---|
| AA:ITA | Copolymer made from a 4:1 mole ratio of acrylic acid:itaconic acid, prepared according to Example 3 of U.S. Pat. No. 5,130,347 (Mitra), MW (average) = 106,000; polydispersity ρ = 4.64. |
| IEM | 2-Isocyanatoethyl methacrylate (Sigma-Aldrich, St. Louis, MO) |
| AA:ITA:IEM | Polymer made by reacting AA:ITA copolymer with sufficient IEM to convert 16 mole percent of the acid groups of the copolymer to pendent methacrylate groups, according to the dry polymer preparation of Example 11 of U.S. Pat. No. 5,130,347. |
| HEMA | 2-Hydroxyethyl methacrylate (Sigma-Aldrich) |
| CPQ | Camphorquinone (Sigma-Aldrich) |
| EDMAB | Ethyl 4-(N,N-dimethylamino)benzoate (Sigma-Aldrich) |
| DPIHFP | Diphenyliodonium Hexafluorophosphate (Alfa Aesar, Ward Hill, MA) |
| PEGDMA 400 | Polyethyleneglycol dimethacrylate (Sartomer, Exton, PA) |

Starting Materials

Compound A
(6-Amino-1-hydroxyhexylidene)bisphosphonic Acid Monosodium Salt)

A 250-ml 3-neck flask was equipped with a mechanical stirrer, dry ice/acetone condenser connected to a caustic scrubber, and a thermocouple. The system was flushed with nitrogen for 20 minutes. Added with continuous stirring at room temperature were 6-aminocaproic acid (52.5 g, 0.40 mol; Sigma-Aldrich), phosphorous acid (32 g, 0.38 mol), and methanesulfonic acid (160 ml). The mixture was heated to 65° C. and then phosphorus trichloride (PCl$_3$, 70 ml, 0.80 mol) was added over 20 minutes using a dropping funnel. Stirring was continued at 65° C. overnight. The clear reaction mixture was cooled to 30° C. and then quenched into 400 ml of ice-cold water. An additional 200 ml of water was used to rinse the reaction flask and then added to the cold mixture. The aqueous mixture was warmed to room temperature and then heated to reflux for 5 hours. The mixture was cooled to 20° C. and the pH was raised to 4.3 using 50 wt.-% aqueous sodium hydroxide. The clear mixture was cooled in an ice bath for 2 hours during which time a white crystalline solid formed. The solid was isolated by vacuum filtration. The filter cake was washed with ice-cold water (2 50-ml portions) and then ethanol (100 ml). The white solid was dried by air for 2 days and then with a vacuum pump overnight to give a white solid in 93% yield. The solid was characterized as (6-amino-1-hydroxyhexylidene)bisphosphonic acid monosodium salt (Compound A) having the following Nuclear Magnetic Resonance (NMR) values: $^1$H NMR (D$_2$O) σ 2.90 (t, 2H), 1.84-1.94 (m, 2H), 1.62-1.70 (m, 2H), 1.53-1.61 (m, 2H), 1.32-1.40 (m, 2H); $^{13}$C NMR σ 74.5 (t), 39.5, 33.5, 26.5 (s+s), 23; $^{31}$P NMR σ 19.5.

Compound B
(4-Amino-1-hydroxybutylidene)bisphosphonic Acid Monosodium Salt)

Compound B was prepared from 4-aminobutyric acid (Sigma-Aldrich) by the same procedure as described for Compound A. A white solid was isolated in 90.8% yield and was characterized as (4-amino-1-hydroxybutylidene)bisphosphonic acid monosodium salt (Compound B) having the following NMR values: $^1$H NMR (D$_2$O) σ 3.0 (m, 2H), 2.0 (m, 4H); $^{13}$C NMR σ 74.5 (t), 41, 32, 24; $^{31}$P NMR σ 19.0 (s).

Compound C
(12-Amino-1-hydroxydodecylidene)bisphosphonic Acid)

A 250-ml flask was fitted with a mechanical stirrer, a thermocouple, an addition funnel, and a reflux condenser with dry ice which was connected to a caustic scrubber. The system was flushed with nitrogen and charged with 12-aminododecanoic acid (21.04 g, 0.098 mol; Advanced Synthesis Technologies, San Ysidro, Calif.), phosphorous acid (8.00 g, 0.098 mol), and methanesulfonic acid (40 ml). The mixture was heated to 65° C., PCl$_3$ (26.83 g, 0.195 mol) was added over 20 min, and the mixture was maintained at 65° C. overnight. The mixture was cooled to 60° C. and water (75 ml) was added dropwise over 30 minutes. The mixture was then heated to reflux for 5 hours. After cooling to 30° C., the flask contents were precipitated with excess water. The solid was filtered, washed several times with water, and air-dried for 2 days to afford a white solid (32 g, 82.5%). The solid was characterized as (12-amino-1-hydroxydodecylidene)bisphosphonic acid (Compound C) having the following NMR values (recorded using a KOH solution of the solid): $^1$H NMR (D$_2$O) σ 2.45 (t, 2H), 1.65-1.80 (m, 2H), 1.35-1.45 (m, 2H), 1.25-1.30 (m, 2H), 1.05-1.20 (m, 14H); $^{13}$C NMR σ 77.1 (t), 40.9, 36.7, 32, 30.8, 29.4 (s+s), 29.0, 28.8 (s+s), 26, 24; $^{31}$P NMR σ 19.5 (s).

Compound D
(11-Amino-1-hydroxyundecylidene)bisphosphonic Acid)

Compound D was prepared from 11-aminoundecanoic acid (Sigma-Aldrich) by the same procedure as described for Compound C. A white solid was isolated in 92.96% yield and was determined to have $^1$H, $^{13}$C, and $^{31}$P NMR values (recorded using a KOH solution of the solid) consistent with the compound (11-amino-1-hydroxyundecylidene)bisphosphonic acid (Compound D).

Example 1

(1-Hydroxy-6-methacrylamidohexylidene)bisphosphonic Acid (Formula II: $R^3$=CH$_3$, $R^4$=H, x=1, $R^2$=OH, and A=(CH$_2$)$_5$)

Sodium hydroxide pellets (46.5 g, 1.16 mol) were dissolved in water (150 ml) in a 500-ml 2-neck flask equipped with a mechanical stirrer. The solution was cooled in an ice bath for 15 minutes. With vigorous stirring, Compound A (50 g, 0.182 mol) was added and the resulting mixture stirred until a clear solution was obtained. To the cold solution was added methacryloyl chloride (21.0 g, 0.200 mol) dropwise over 10 minutes. The mixture was vigorously stirred in the ice bath for 3 hours (pH above 9). The mixture was acidified using concentrated HCl until pH paper indicated a pH value below 2. Methanol (500 ml) was added and the precipitated solid (NaCl) was removed by vacuum filtration. The filtrate was concentrated in a rotary evaporator and the obtained residue was dissolved in methanol (200 ml). The resulting cloudy solution was filtered through a celite bed and the clear filtrate was concentrated in a rotary evaporator to afford a solid that was dried in a vacuum pump at 40° C. overnight to give a white solid quantitatively (i.e., 100% yield). The solid was characterized as (1-hydroxy-6-methacrylamidohexylidene)

bisphosphonic acid (Example 1) having the following NMR values: $^1$H NMR (D$_2$O) σ 5.65 (s, 1H), 5.35 (s, 1H), 3.2 (t, 2H), 1.95-2.05 (m, 2H), 1.9 (s, 3H), 1.65-1.75 (m, 2H), 1.5-1.6 (m, 2H), 1.25-1.35 (m, 2H); $^{13}$C NMR σ 171, 141, 121, 74 (t), 41, 35, 31, 29, 24, 19; $^{31}$P NMR (single peak, not referenced).

The hydrolytic stability of Example 1 was demonstrated by aging in water for 5 months at 45° C. without any detectable hydrolysis (based on $^{31}$P NMR) being observed.

Example 1A (1-Hydroxy-6-acrylamidohexylidene)bisphosphonic Acid (Formula II: R$^3$=H, R$^4$=H, x=1, R$^2$=OH, and A=(CH$_2$)$_5$)

(1-Hydroxy-6-acrylamidohexylidene)bisphosphonic acid (white solid, Example 1A) was prepared and characterized as described for Example 1, except that acryloyl chloride was substituted for methacryloyl chloride.

Example 2

(1-Hydroxy-4-methacrylamidobutylidene)bisphosphonic Acid (Formula II: R$^3$=CH$_3$, R$^4$=H, x=1, R$^2$=OH, and A=(CH$_2$)$_3$)

Example 2 was prepared from Compound B by the same procedure as described for Example 1. A white solid was isolated in 74.8% yield and was characterized as (1-hydroxy-4-methacrylamidobutylidene)bisphosphonic acid (Example 2) having the following NMR values: $^1$H NMR (D$_2$O) σ 5.55 (s, 1H), 5.30 (s, 1H), 3.15 (t, 2H), 1.85-2.00 (m, 2H), 1.80 (s, 3H), 1.70-1.80 (m, 2H); $^{13}$C NMR σ 172, 139, 121, 74 (t), 40, 31, 24, 18; $^{31}$P NMR σ 20.4 (s)

Example 3

(1-Hydroxy-12-methacrylamidododecylidene)bisphosphonic Acid (Formula II: R$^3$=CH$_3$, R$^4$=H, x=1, R$^2$=OH, and A=(CH$_2$)$_{11}$)

Potassium hydroxide pellets (19.75 g, 0.35 mol) were dissolved in water (60 ml) in a 500 ml 2-neck flask equipped with a mechanical stirrer. Compound C (20.0 g, 0.05 mol) was added and stirring was continued until a clear solution was obtained. The flask was cooled in an ice bath for 15 minutes. Methacryloyl chloride (5.90 g, 0.055 mol) was added dropwise to the cold solution with vigorous stirring over 10 minutes. The mixture was stirred for 3 hours in the ice bath and concentrated hydrochloric acid was added slowly and dropwise until the mixture became acidic (about 21.5 mol of concentrated HCl were used). The separated solid was filtered by vacuum filtration. The filter cake was washed several times with water and then air dried over night. A white solid was isolated in 90.85% yield and was determined to have $^1$H, $^{13}$C, and $^{31}$P NMR values (recorded using a KOH solution of the solid) consistent with the compound (1-hydroxy-12-methacrylamidododecylidene)bisphosphonic acid (Example 3).

Example 4

(1-Hydroxy-11-methacrylamidoundecylidene)bisphosphonic Acid (Formula II: R$^3$=CH$_3$, R$^4$=H, x=1, R$^2$=OH, and A=(CH$_2$)$_{10}$)

Example 4 was prepared from Compound D by the same procedure as described for Example 3. A white solid was isolated in 78.95% yield and was determined to have $^1$H, $^{13}$C, and $^{31}$P NMR values (recorded using a KOH solution of the solid) consistent with the compound (1-hydroxy-11-methacrylamidoundecylidene)bisphosphonic acid (Example 4).

Example 5

(Methylidene Methanebisphosphonic Acid) (Formula I: R$^1$ and R$^2$ are CH$_3$CH=)

General Synthetic Procedure A

Tetraalkyl methanebisphosphonates react with aliphatic and aromatic aldehydes to produce tetraalkyl alkylidene and arylidene methanebisphosphonates (Formula I where R$^1$ and R$^2$ form a double bond with the central carbon of the P—C—P group and with alkyl groups on the 4 P—OH groups). The resulting tetraalkyl alkylidene and arylidene methanebisphosphonates can be hydrolyzed in acid to yield the corresponding alkylidene and arylidene methanebisphosphonic acids.

Following the General Synthetic Procedure A, acetaldehyde is reacted with tetramethyl methanebisphosphonate to produce tetramethyl methylidene methanebisphosphonate that is then hydrolyzed to yield methylidene methanebisphosphonic acid. (Formula I where R$^1$ and R$^2$ form a CH$_3$CH= link to the central carbon of the P—C—P group.)

Example 6

(4-Methacrylamidobutylidene Methanebisphosphonic Acid) (Formula I: R$^1$ and R$^2$ are CH$_2$=C(CH$_3$)C(O)NH(CH$_2$)$_3$CH=)

Following the General Synthetic Procedure A, 4-nitrobutanal is reacted with tetramethyl methanebisphosphonate to produce tetramethyl 4-nitrobutylidene methanebisphosphonate that is then hydrogenated to reduce the nitro group to an amine group, and then hydrolyzed to yield 4-aminobutylidene methanebisphosphonic acid. The resulting acid is then methacrylated with methacryloyl chloride to afford 4-methacrylamidobutylidene methanebisphosphonic acid.

Example 7

(4-Vinylbenzyl-methanebisphosphonic Acid) (Formula I: R$^1$ is 4-vinylbenzyl and R$^2$ is H)

General Synthetic Procedure B

Tetraalkyl methanebisphosphonates react with aliphatic and aromatic halides (e.g., chlorides, bromides, and iodides) to produce tetraalkyl alkyl- and aryl- methanebisphosphonates (Formula I where R$^1$ is alkyl or aryl, R$^2$ is H, and with alkyl groups on the 4 P—OH groups). The resulting tetraalkyl alkyl- and aryl-methanebisphosphonates can be hydrolyzed in acid to yield the corresponding alkyl- and aryl-methanebisphosphonic acids.

Following the General Synthetic Procedure B, 4-vinylbenzylchloride is reacted with tetramethyl methanebisphosphonate to produce tetramethyl 4-vinylbenzyl-methanebisphosphonate that is then hydrolyzed to yield 4-vinylbenzyl-methanebisphosphonic acid.

Example 8

(6-Methacryloxyhexyl-methanebisphosphonic Acid) (Formula I: R$^1$ is 6-methacryloxyhexyl and R$^2$ is H)

Following the General Synthetic Procedure B, methyl 6-chlorohexanoate is reacted with tetramethyl methanebisphosphonate to produce tetramethyl 5-methoxycarbonyl-pentyl-methanebisphosphonate that is then hydrolyzed to yield 5-carboxypentyl-methanebisphosphonic acid, and then hydrogenated to reduce the carboxy group to a hydroxymethylene group. The resulting 6-hydroxyhexyl-methanebisphosphonic acid is then methacrylated with methacryloyl chloride to afford 6-methacryloxyhexyl-methanebisphosphonic acid.

Example 9

(1,3-Bis(methacrylamido)butane-1,1-bisphosphonic Acid) (Formula II: $R^2$ is $NHCOCCH_3=CH_2$, $R^3$ is $CH_3$, $R^4$ is H, and A is $—CH(CH_3)CH_2—$)

The starting material 1,3-diamino-butane-1,1-bisphosphonic acid can be prepared by the reaction of 3-aminobutyronitrile with phosphorus-tribromide in dioxane followed by hydrolysis and crystallization according to the following procedure. 3-Aminobutyronitrile (21 g, 0.25 mol) is dissolved in 100 ml dioxane and is reacted with phosphorus-tribromide (135.5 g, 0.5 mol) at 30° C. for 24 hours. Water is added (27 g, 1.5 mol) and the mixture is heated to 65° C. for 3 hours. After addition of 100 g water, dioxane is distilled off, and the product (1,3-diaminobutane-1,1-bisphosphonic acid) crystallizes from the residue during cooling to 20° C. After separation by filtration, the product is washed several times with small amounts of cold water and then dried in a vacuum at 110° C. Yield 9.1 g (15% theory). Melting point 255° C.

Example 9 (1,3-bis(methacrylamido)butane-1,1-bisphosphonic Acid) can be prepared by the reaction of 1,3-diaminobutane-1,1-bisphosphonic acid with methacryloyl chloride according to the following procedure.

Sodium hydroxide pellets (28.0 g, 0.70 mol) are dissolved in water (90 ml) in a 250-ml 2-neck flask equipped with a mechanical stirrer. The resulting solution is cooled in an ice bath for 15 minutes. With vigorous stirring, 1,3-diaminobutane-1,1-bisphosphonic acid (24.81 g, 0.100 mol) is added and the resulting mixture is stirred for one hour. To the cold solution is added methacryloyl chloride (23.0 g, 0.220 mol) dropwise over 10 minutes. The mixture is vigorously stirred in the ice bath for 3 hours. The mixture is acidified using concentrated HCl until pH paper indicates a pH value below 2. Methanol (300 ml) is added and the resulting solid precipitate is removed by filtration. The filtrate is concentrated in a rotary evaporator and the residue is dissolved in methanol (120 ml). The solution is filtered again and the filtrate is concentrated in a rotary evaporator to afford solid that is dried under vacuum. The dried solid is characterized as 1,3-bis(methacrylamido)butane-1,1-bisphosphonic acid (Example 9).

Examples 10-13

Compositions and Evaluations

The compositions of the present invention were prepared by the following general procedure. A solid bisphosphonic acid derivative (e.g., Example 1 or 1A) was first weighed into a clear glass vial followed by the addition of water, optionally a polymerizable component, and optionally other ingredients, such as, additional polymerizable components, surfactants, salts, and initiators. Once all of the components had been added, the vial was tightly capped and vigorously shaken by hand for about 30 seconds. Based on visual observations, the resulting compositions were clear, homogeneous solutions. Following mixing, the compositions were transferred into an opaque vial for evaluation according to the Shear Bond Strength Test Method described herein.

The compositions prepared in this manner are listed in Table 1 along with the optional adhesives utilized in the Test Method and the results obtained for shear bond strength to enamel and dentin. Negative controls were run for comparison and included SINGLEBOND Adhesive only (Control 1) and SCOTCHBOND Multipurpose Plus Adhesive only (Control 2). The results of these two Controls showed relatively low adhesion for adhesives applied to an enamel or dentin surface that had not been treated with an etchant-containing material. Example 12 is noted as an example of a self-etching adhesive composition, in that it was used as both an etchant and an adhesive to treat the tooth surface before curing and adherence of the composite material.

Tooth Surface Evaluation by Scanning Electron Microscopy (SEM)

Selected bisphosphonic acid derivatives of the present invention could be shown by Scanning Electron Microscopy (SEM) to etch the enamel surface of a tooth. For example, the self-etching primer composition Example 11 was applied to an enamel tooth surface prepared using 320-grit sandpaper. The composition was allowed to remain for 20 seconds and then rinsed off the surface with distilled water. The tooth surface was dried and scanned using standard SEM techniques. The SEM image showed an etched pattern on the treated enamel.

TABLE 1

| Primer Composition | | | Adhesive (Applied After Primer) | Shear Bond Strength (MPa) | |
|---|---|---|---|---|---|
| Ex. | Component | Wt.-% | | Enamel | Dentin |
| 10 | Example 1 | 7.5 | SINGLEBOND Adhesive (3M Company) | 27.7 ± 2.3 | 11.9 ± 4.0 |
|  | HEMA | 42.5 | | | |
|  | Water | 50 | | | |
| 11 | Example 1 | 7.5 | SCOTCH-BOND Multipurpose Plus Adhesive (3M Company) | 34.2 ± 3.6 | 3.0 ± 1.5 |
|  | PEGDMA 400 | 5 | | | |
|  | HEMA | 37.5 | | | |
|  | Water | 50 | | | |
| 12 | Example 1 | 7.5 | None | 23.4 ± 6.7 | 2.2 ± 2.2 |
|  | PEGDMA 400 | 5 | | | |
|  | HEMA | 45.5 | | | |
|  | CPQ | 0.8 | | | |
|  | EDMAB | 0.65 | | | |
|  | DPIHFP | 0.55 | | | |
|  | Water | 40 | | | |
| 13 | Example 1A | 7.5 | SINGLEBOND Adhesive | 20.4 ± 5.6 | 7.5 ± 3.9 |
|  | HEMA | 42.5 | | | |
|  | Water | 50 | | | |
| Control 1 | None | — | SINGLEBOND Adhesive | 4.3 ± 1.4 | 2.2 ± 2.6 |
| Control 2 | None | — | SCOTCH-BOND Multipurpose Plus Adhesive | 6.5 ± 0.9 | 0.6 ± 0.9 |

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by

What is claimed is:

1. A method of treating a hard surface, the method comprising:

etching the hard surface with a composition comprising a compound of the following Formula II:

$$\text{(H}_2\text{C}=\underset{R^3}{\overset{}{C}}-\underset{}{\overset{O}{\underset{\|}{C}}}-\underset{R^4}{\overset{}{N}})_x-A-\underset{\underset{O=\overset{}{\underset{|}{P}}-OH}{|}}{\overset{O=\overset{}{\underset{|}{P}}-OH}{\overset{|}{C}}}-R^2 \quad (II)$$

or a salt thereof, wherein:

x=1-3;

$R^2$ is OH or a (C1-C4)alkoxy group;

each $R^3$ is independently H or $CH_3$;

each $R^4$ is independently H or an alkyl group having a 4 to 18 carbon atoms; and A is a straight chain alkyl group having up to 20 carbon atoms;

with the proviso that the hard surface is not pretreated.

2. The method of claim 1 wherein the composition etches and primes the hard surface.

3. The method of claim 2 wherein the hard surface is a hard tissue.

4. The method of claim 1, wherein the hard surface is a tooth surface; and with the proviso that the tooth surface is not pretreated with phosphoric acid.

5. The method of claim 4 wherein the composition further comprises at least one polymerizable component different from the compound of Formula II.

6. The method of claim 5 wherein the composition functions as a self-etching primer thereby etching and priming the tooth surface simultaneously.

7. The method of claim 5 wherein the composition functions as a self-etching adhesive to promote adherence of a dental material to the tooth surface.

8. The method of claim 7 wherein the dental material is selected from the group consisting of a composite, a filling, a sealant, an inlay, an onlay, a crown, and a bridge.

9. The method of claim 5 wherein the composition functions to promote the adherence of an orthodontic adhesive to the tooth surface, wherein the orthodontic adhesive functions to adhere an orthodontic appliance to the tooth surface.

10. The method of claim 9 wherein the orthodontic appliance is selected from the group consisting of a bracket, a buccal tube, a band, a cleat, a button, a lingual retainer, and a bite blocker.

11. The method of claim 4 further comprising a step of priming the tooth surface.

12. The method of claim 4 further comprising a step of applying a dental adhesive to the tooth surface.

13. The method of claim 4 wherein the tooth surface comprises enamel.

14. The method of claim 4 wherein the tooth surface comprises dentin.

15. A method of adhering an orthodontic appliance to a tooth surface, the method comprising:

etching the tooth surface with a composition comprising a compound of the following Formula II:

$$\text{(H}_2\text{C}=\underset{R^3}{\overset{}{C}}-\underset{}{\overset{O}{\underset{\|}{C}}}-\underset{R^4}{\overset{}{N}})_x-A-\underset{\underset{O=\overset{}{\underset{|}{P}}-OH}{|}}{\overset{O=\overset{}{\underset{|}{P}}-OH}{\overset{|}{C}}}-R^2 \quad (II)$$

or a salt thereof, wherein:

x=1-3;

$R^2$ is OH or a (C1-C4)alkoxy group;

each $R^3$ is independently H or $CH_3$;

each $R^4$ is independently H or an alkyl group having 4 to 18 carbon atoms; and A is a straight chain alkyl group having up to 20 carbon atoms; and adhering an orthodontic appliance to the tooth surface.

16. The method of claim 15 further comprising adhering an orthodontic adhesive to the tooth surface.

17. The method of claim 16 wherein the orthodontic adhesive has been pre-applied to the orthodontic appliance before adhering to the tooth surface.

18. The method of claim 15 wherein the orthodontic appliance is selected from the group consisting of a bracket, a buccal tube, a band, a cleat, a button, a lingual retainer, and a bite blocker.

19. The method of claim 15 further comprising a step of priming the tooth surface prior to adhering an orthodontic appliance to the tooth surface.

20. The method of claim 19 wherein the composition further comprises at least one polymerizable component different from the compound of Formula II and wherein the steps of etching and priming are done simultaneously with the composition functioning as a self-etching primer composition.

21. The method of claim 20 further comprising adhering an orthodontic adhesive to the tooth surface.

22. The method of claim 21 wherein the orthodontic adhesive has been pre-applied to the orthodontic appliance before adhering to the tooth surface.

23. The method of claim 15 further comprising a step of applying a dental adhesive to the tooth surface prior to adhering an orthodontic appliance to the tooth surface.

24. The method of claim 23 wherein the composition further comprises at least one polymerizable component different from the compound of Formula II and wherein the steps of etching and applying a dental adhesive are done simultaneously with the composition acting as a self-etching adhesive composition.

25. The method of claim 24 further comprising adhering an orthodontic adhesive to the tooth surface.

26. The method of claim 25 wherein the orthodontic adhesive has been pre-applied to the orthodontic appliance before adhering to the tooth surface.

27. An etching composition comprising:

an ethylenically unsaturated polymerizable component; and a compound of Formula II, which is different from the polymerizable component, wherein Formula II is:

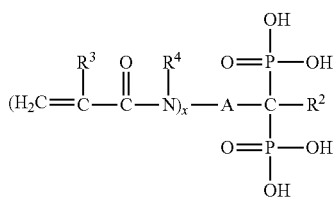

(II)

or a salt thereof, wherein:
x=1-3;
R² is OH or a (C1-C4)alkoxy group;
each R³ is independently H or CH₃;
each R⁴ is independently H or an alkyl group having 4 to 18 carbon atoms; and
A is a straight chain alkyl group having up to 20 carbon atoms;
wherein the compound of Formula II is present in an amount sufficient to etch a hard surface, thereby forming an etchant.

28. The composition of claim 27 wherein the composition is a self-etching primer.

29. The composition of claim 27 wherein the composition is a self-etching adhesive.

30. The composition of claim 27 wherein each R⁴ is independently a (C8-C18)alkyl group.

31. The composition of claim 27 wherein R² is a (C1-C4) alkoxy group.

32. The composition of claim 27 wherein R² is OH.

33. The composition of claim 27 wherein A is (CH₂)ₙ wherein n=6-20.

34. The composition of claim 33 wherein n=10-20.

35. The composition of claim 27 wherein the compound of Formula II is present in an amount of at least about 1 wt-%, based on the total weight of the composition.

36. The composition of claim 27 wherein the polymerizable component is selected from the group consisting of 2-hydroxyethyl methacrylate (HEMA), polyethyleneglycol dimethacrylate (PEGDMA), copolymer of acrylic acid:itaconic acid with pendent methacrylate (AA:ITA:IEM), 2,2-bis [4-(2-hydroxy-3-methacryloxypropoxy)phenyl]propane (bisGMA), urethane dimethacrylate (UDMA) glycerol dimethacrylate (GDMA), and combinations thereof.

37. The composition of claim 27 further comprising an adhesive component.

38. The composition of claim 27 further comprising a primer component.

39. The composition of claim 27 further comprising a filler.

40. The composition of claim 27 further comprising water or a nonaqueous solvent.

41. The composition of claim 27 further comprising a photoinitiator.

42. The composition of claim 27 further comprising an oxidizing agent and a reducing agent.

43. The composition of claim 27 wherein the hard surface is dentin or enamel.

* * * * *

UNITED STATES PATENT AND TRADEMARK OFFICE
CERTIFICATE OF CORRECTION

PATENT NO. : 8,404,144 B2
APPLICATION NO. : 12/275954
DATED : March 26, 2013
INVENTOR(S) : Ahmed S Abuelyaman It is certified that error appears in the above-identified patent and that said Letters Patent is hereby corrected as shown below:

On Title page 3, item 56

Column 1 (Other Publications)
Line 17, Delete "Ionomer/Composite" and insert -- Ionomer/Composite --, therefor.

Column 2 (Other Publications)
Line 17, Delete "May 5," and insert -- May 15, --, therefor.
Line 51, Delete "Sufur" and insert -- Sulfur --, therefor.
Line 52, Delete "Catonic" and insert -- Cationic --, therefor.
Line 54, Delete "Aminonapthtothiazoles"," and insert -- Aminonaphthothiazoles", --, therefor.

In the Specifications

Column 1
Line 60, Delete "TI" and insert -- II --, therefor.

Column 8
Line 39, Delete "bisphenolA" and insert -- bisphenol A --, therefor.

Column 9
Line 5, Delete "Rhom" and insert -- Rohm --, therefor.

Column 10
Line 22, Delete "2,3-bomanedione" and insert -- 2,3-bornanedione --, therefor.

Column 11
Line 35, Delete "Tonomer/" and insert -- Ionomer/ --, therefor.

Signed and Sealed this
Seventeenth Day of December, 2013

Margaret A. Focarino
*Commissioner for Patents of the United States Patent and Trademark Office*

Column 13
Line 36, Delete "unimodial or polymodial" and insert -- unimodal or polymodal --, therefor.

Column 19
Line 56, Delete "NMR 6" and insert -- NMR σ --, therefor.

Column 21
Line 13, Delete "R=H, $R^4$=H, x=1, R=OH," and insert -- $R^3$=$CH_3$, $R^4$=H, x=1, $R^2$=OH, --, therefor.

In the Claims

Column 25
Line 24, In Claim 1, after "having" delete "a".

Column 28
Line 14, In Claim 36, delete "(UDMA)" and insert -- (UDMA), --, therefor.